(12) United States Patent
Leonhardt

(10) Patent No.: US 11,471,686 B2
(45) Date of Patent: *Oct. 18, 2022

(54) KLOTHO MODULATION

(71) Applicant: Leonhardt Ventures LLC, Corona Del Mar, CA (US)

(72) Inventor: Howard J. Leonhardt, Playa Vista, CA (US)

(73) Assignee: Leonhardt Ventures LLC, Mission Viejo, CA (US)

( * ) Notice: Subject to any disclaimer, the term of this patent is extended or adjusted under 35 U.S.C. 154(b) by 511 days.

This patent is subject to a terminal disclaimer.

(21) Appl. No.: 16/352,756

(22) Filed: Mar. 13, 2019

(65) Prior Publication Data

US 2020/0289826 A1 Sep. 17, 2020

(51) Int. Cl.
*A61N 1/36* (2006.01)
*A61N 1/04* (2006.01)
(Continued)

(52) U.S. Cl.
CPC ......... *A61N 1/36153* (2013.01); *A61N 1/044* (2013.01); *A61N 1/0464* (2013.01); *A61N 1/0468* (2013.01); *A61N 1/326* (2013.01); *A61N 1/3601* (2013.01); *A61N 1/36002* (2017.08); *A61N 1/36003* (2013.01); *A61N 1/36007* (2013.01); *A61N 1/3616* (2013.01); *A61N 1/36021* (2013.01); *A61N 1/36025* (2013.01); *A61N 1/36034* (2017.08); *A61N 1/36157* (2013.01); *A61N 1/36167* (2013.01); *A61N 1/36171* (2013.01); *A61N 1/36175* (2013.01);
(Continued)

(58) Field of Classification Search
CPC .. A61N 1/36153; A61N 1/044; A61N 1/0464; A61N 1/0468; A61N 1/326; A61N 1/36002; A61N 1/36003; A61N 1/36007; A61N 1/3601; A61N 1/36021; A61N 1/36025; A61N 1/36034; A61N 1/36157; A61N 1/3616; A61N 1/36167; A61N 1/36171; A61N 1/36175; A61N 1/36178; A61N 2001/083; A61N 1/0408; A61N 1/0492
See application file for complete search history.

(56) References Cited

U.S. PATENT DOCUMENTS

D263,073 S 2/1982 Jonkers et al.
D273,893 S 5/1984 Weitzman
(Continued)

FOREIGN PATENT DOCUMENTS

CA 2685161 A1 10/2007
EP 0603451 A1 6/1994
(Continued)

OTHER PUBLICATIONS

Chen et al. "Secreted Klotho Attenuates Inflammation-Associated Aortic Valve Fibrosis in Senescence-Accelerated Mice P1" Hypertension May 2018; 71:877-885.
(Continued)

*Primary Examiner* — Eugene T Wu
(74) *Attorney, Agent, or Firm* — TraskBritt

(57) ABSTRACT

Described is a low voltage, pulsed electrical stimulation device for controlling expression of klotho, a useful protein, by tissues. Also described are methods of enhancing expression of klotho in cells.

21 Claims, 13 Drawing Sheets

(51) Int. Cl.
    *A61N 1/32* (2006.01)
    *A61N 1/08* (2006.01)
(52) U.S. Cl.
    CPC .... *A61N 1/36178* (2013.01); *A61N 2001/083* (2013.01)

(56) References Cited

U.S. PATENT DOCUMENTS

| | | | |
|---|---|---|---|
| 4,622,952 A | 11/1986 | Gordon | |
| 4,976,733 A | 12/1990 | Girardot | |
| 5,211,622 A | 5/1993 | Liboff et al. | |
| 5,295,958 A | 3/1994 | Shturman | |
| 5,543,318 A | 8/1996 | Smith et al. | |
| 5,693,029 A | 12/1997 | Leonhardt | |
| 5,713,917 A | 2/1998 | Leonhardt et al. | |
| 5,725,377 A | 3/1998 | Lemler et al. | |
| 5,817,139 A | 10/1998 | Kasano | |
| 5,957,949 A | 9/1999 | Leonhardt et al. | |
| 6,344,052 B1 | 2/2002 | Greenan et al. | |
| 6,618,625 B2 | 9/2003 | Silverstone | |
| 6,957,106 B2 | 10/2005 | Schuler et al. | |
| 6,988,004 B2 | 1/2006 | Kanno et al. | |
| 7,029,276 B2 | 4/2006 | Mao | |
| 7,136,699 B2 | 11/2006 | Palti | |
| 7,341,062 B2 | 3/2008 | Chachques et al. | |
| 7,483,749 B2 | 1/2009 | Leonhardt et al. | |
| 7,686,799 B2 | 3/2010 | Leonhardt et al. | |
| 7,881,784 B2 | 2/2011 | Pasricha et al. | |
| 8,041,428 B2 | 10/2011 | Errico et al. | |
| 8,133,267 B2 | 3/2012 | Leonhardt et al. | |
| 8,166,976 B2 | 5/2012 | Webster et al. | |
| 8,226,407 B2 | 7/2012 | Hanewinkel et al. | |
| 8,465,533 B2 | 6/2013 | Palti | |
| 8,534,289 B2 | 9/2013 | Hernandez | |
| 8,639,361 B2 | 1/2014 | Nathanson | |
| 8,646,455 B2 | 2/2014 | Webster et al. | |
| 8,656,930 B2 | 2/2014 | Schuler et al. | |
| 8,660,669 B2 | 2/2014 | Nemeh et al. | |
| 8,738,144 B2 | 5/2014 | Schneider | |
| 8,909,346 B2 | 12/2014 | Chalmers | |
| 8,945,104 B2 | 2/2015 | Boone et al. | |
| 9,032,964 B2 | 5/2015 | Schuler et al. | |
| 9,173,811 B2 | 11/2015 | Greiner et al. | |
| 9,533,170 B2 | 1/2017 | Dye et al. | |
| 9,545,331 B2 | 1/2017 | Ingemarsson-Matzen | |
| D778,449 S | 2/2017 | Ingemarsson-Matzen | |
| 9,656,096 B2 | 5/2017 | Pilla | |
| 9,662,184 B2 | 5/2017 | Lowe | |
| 9,687,383 B2 | 6/2017 | Ingemarsson-Matzen | |
| 9,707,403 B2 | 7/2017 | Schuler | |
| 9,855,418 B2 | 1/2018 | Haralambidis | |
| 9,987,326 B2 | 6/2018 | Koeffler et al. | |
| D832,447 S | 10/2018 | Wiffen | |
| 10,543,119 B2 | 1/2020 | Ingemarsson-Matzen | |
| D881,399 S | 4/2020 | Ingemarsson-Matzen | |
| 10,646,644 B2 | 5/2020 | Leonhardt et al. | |
| 10,960,206 B2 | 3/2021 | Leonhardt et al. | |
| 11,058,536 B2 | 7/2021 | Huber | |
| 11,110,274 B2 | 9/2021 | Leonhardt | |
| 2002/0143373 A1 | 10/2002 | Courtnage et al. | |
| 2003/0032998 A1 | 2/2003 | Altman | |
| 2003/0220556 A1 | 11/2003 | Porat et al. | |
| 2004/0010231 A1 | 1/2004 | Leonhardt et al. | |
| 2004/0115587 A1 | 6/2004 | Breining et al. | |
| 2004/0147906 A1 | 7/2004 | Voyiazis et al. | |
| 2004/0236238 A1 | 11/2004 | Schuler et al. | |
| 2005/0171578 A1 | 8/2005 | Leonhardt | |
| 2006/0030908 A1 | 2/2006 | Powell et al. | |
| 2006/0100553 A1 | 5/2006 | Lodin | |
| 2007/0123758 A1 | 5/2007 | Miesel et al. | |
| 2007/0167984 A1 | 7/2007 | Kieval et al. | |
| 2007/0190028 A1 | 8/2007 | Qu et al. | |
| 2007/0265680 A1 | 11/2007 | Liu et al. | |
| 2008/0227046 A1 | 9/2008 | Lowe et al. | |
| 2008/0243060 A1 | 10/2008 | Hartmann et al. | |
| 2009/0132010 A1 | 5/2009 | Kronberg | |
| 2009/0240304 A1* | 9/2009 | Blum | A61N 1/326 607/48 |
| 2010/0082027 A1 | 4/2010 | Chalmers | |
| 2010/0184183 A1 | 7/2010 | Schussler et al. | |
| 2012/0156648 A1 | 6/2012 | Kaufman et al. | |
| 2013/0253413 A1 | 9/2013 | Levine et al. | |
| 2014/0023983 A1 | 1/2014 | Lowe et al. | |
| 2014/0214115 A1 | 7/2014 | Greiner et al. | |
| 2014/0214116 A1 | 7/2014 | Peterson et al. | |
| 2014/0214124 A1 | 7/2014 | Greiner et al. | |
| 2014/0214144 A1 | 7/2014 | Peterson et al. | |
| 2014/0228910 A1 | 8/2014 | Schuler et al. | |
| 2017/0028184 A1 | 2/2017 | Godden et al. | |
| 2017/0036032 A1 | 2/2017 | Schuler et al. | |
| 2017/0112983 A1 | 4/2017 | Thorne et al. | |
| 2017/0266371 A1* | 9/2017 | Leonhardt | A61N 1/326 |
| 2017/0274206 A1 | 9/2017 | Leonhardt | |
| 2018/0043159 A1 | 2/2018 | Hassan et al. | |
| 2018/0064935 A1 | 3/2018 | Leonhardt et al. | |
| 2018/0071135 A1 | 3/2018 | Ingemarsson-Matzen | |
| 2018/0193646 A1* | 7/2018 | Fostick | A61N 1/0531 |
| 2019/0015661 A1 | 1/2019 | Leonhardt et al. | |
| 2019/0022389 A1 | 1/2019 | Leonhardt | |
| 2019/0022396 A1 | 1/2019 | Leonhardt | |
| 2019/0125932 A1 | 5/2019 | Leonhardt et al. | |
| 2019/0255321 A1* | 8/2019 | Planard-Luong | H03K 7/08 |
| 2019/0290541 A1 | 9/2019 | Greiner et al. | |
| 2020/0030136 A1 | 1/2020 | Hernandez | |
| 2020/0324106 A1 | 10/2020 | Leonhardt | |
| 2020/0330753 A1 | 10/2020 | Leonhardt et al. | |
| 2021/0228870 A1 | 7/2021 | Leonhardt | |

FOREIGN PATENT DOCUMENTS

| | | |
|---|---|---|
| JP | 2013-034881 A | 2/2013 |
| KR | 10-2007-0010908 A | 1/2007 |
| KR | 10-0726825 B1 | 6/2007 |
| WO | 92/17118 A1 | 10/1992 |
| WO | 2006/116728 A2 | 11/2006 |
| WO | 2007/146187 A2 | 12/2007 |
| WO | 2008/145724 A1 | 12/2008 |
| WO | 2009/021535 A1 | 2/2009 |
| WO | 2011/016629 A2 | 2/2011 |
| WO | 2014/172693 A2 | 1/2014 |
| WO | 2016/135295 A1 | 9/2016 |
| WO | 2017/142948 A1 | 8/2017 |

OTHER PUBLICATIONS

Klotho et al. "Klotho expression in osteocytes regulates bone metabolism and controls bone formation" Kidney International (2017) 92, 599-611.

Andringa et al. "Role of Hypoxia-Inducible Factors in Acute Kidney Injury" Nephron Clin Pract (Sep. 2014) 127: 70-74; doi.org/10.1159/000363669.

Dalton et al. "New Insights into the Mechanism of Action of Soluble Klotho." Frontiers in endocrinology vol. 8 323. Nov. 17, 2017, doi:10.3389/fendo.2017.00323.

Dërmaku-Sopjani et al. "Significance of the anti-aging protein Klotho" Molecular Membrane Biology, 30:8, 369-385 (Aug. 2013), DOI: 10.3109/09687688.2013.837518.

Drew et al. "Association between Soluble Klotho and Change in Kidney Function: The Health Aging and Body Composition Study" J Am Soc Nephrol Jun. 2017,28(6):1859-1866; DOI: doi.org/10.1681/ASN.2016080828.

Floege et al. "A New Look at Platelet-Derived Growth Factor in Renal Disease" J Am Soc Nephrol (Jan. 2008), 19(1):12-23; DOI: doi.org/10.1681/ASN.2007050532.

Fu et al. "Loss of Klotho in CKD Breaks One's Heart" J Am Soc Nephrol Oct. 2015, 26 (10) 2305-2307; DOI: https://doi.org/10.1681/ASN.2015020200.

Golembiewska et al. "The Role of Klotho Protein in Chronic Kidney Disease: Studies in Animals and Humans" Current Protein & Peptide Science vol. 17, Issue 8, 2016; DOI: 10.2174/1389203717666160526123646.

(56) References Cited

OTHER PUBLICATIONS

Grange et al. "Urinary Extracellular Vesicles Carrying Klotho Improve the Recovery of Renal Function in an Acute Tubular Injury Mode" Molecular Therapy vol. 28 No. 2 490-502 (Feb. 2020) (with Supplemental Information) https://doi.org/10.1016/j.ymthe.2019.11.013.
Gutierrez et al. "a-Klotho and Kidney Function Decline: An Important Step Forward in Understanding the Link Between Mineral Metabolism and Kidney Disease Progression" Am J Kidney Dis. (Jun. 2013) 61(6):855-857.
Hasegawa et al. "Recent advances in renal regeneration." F1000Research vol. 8 F1000 Faculty Rev-216. Feb. 25, 2019, doi:10.12688/f1000research.17127.1.
Hu et al. "Recombinant a-Klotho may be prophylactic and therapeutic for acute to chronic kidney disease progression and uremic cardiomyopathy" Kidney International Basic Research vol. 91, Issue 5, p. 1104-1114 (Jan. 2017); DOI:https://doi.org/10.1016/j.kint.2016.10.034.
Hu et al. "Secreted klotho and chronic kidney disease" Advances in Experimental Medicine and Biology, Jan. 1, 2012, 728:126-157; DOI: 10.1007/978-1-4614-0887-1_9.
Jorge et al. "Klotho deficiency aggravates sepsis-related multiple organ dysfunction" Am J Physiol Renal Physiol 316: F438-F448, (Dec. 5, 2018); doi:10.1152/ajprenal.00625.2017.
Kuro-O "The Klotho proteins in health and disease" Nat Rev Nephrol 15, 27-44 (Nov. 19, 2018) doi.org/10.1038/S41581-018-0078-3.
Lu et al. "Klotho/FGF23 Axis in Chronic Kidney Disease and Cardiovascular Disease" Kidney Dis (Jul. 2017) 3:15-23; doi.org/10.1159/000452880.
Mitani et al. "In Vivo klotho Gene Transfer Ameliorates Angiotensin II-Induced Renal Damage" Hypertension (Apr. 2002) 39:838-843; https://doi.org/10.1161/01.HYP.0000013734.33441.EA.
Mostafidi et al. "Serum Klotho Levels in Trained Athletes", Nephro-Urol Mon. (Jan. 2016); 8(1):e30245. doi:10.5812/numonthly.30245.
Pastor et al. "Treating Systemic Klotho Deficiency" Am J Nephrol (Apr. 2019) 49:410-412; doi.org/10.1159/000499864.
Seo et al. "Renal Klotho expression in patients with acute kidney injury is associated with the severity of the injury" The Korean Journal of Internal Medicine (Jul. 2015);30(4):489-495.
Takenaka et al. "[OP.4B.02] Klotho Supplementation Attenuates Blood Pressure and Oxidative Stress in Diabetes" Journal of Hypertension Sep. 2017—vol. 35—Issue—p. e38; doi: 10.1097/01.hjh.0000523076.42214.98.
Takenaka et al. "Klotho Ameliorates Medullary Fibrosis and Pressure Natriuresis in Hypertensive Rat Kidneys." Hypertension (Dallas, Tex.: 1979) vol. 72,5 (Nov. 2018): 1151-1159 doi:10.1161/HYPERTENSIONAHA.118.1117.
Vervloet et al. "Fibroblast growth factor-23 and Klotho in chronic kidney disease" Kidney International Supplements vol. 1, Issue4, p. 130-135, Sep. 1, 2011;DOI: https://doi.org/10.1038/kisup.2011.29.
Wang et al. "Correlation between Soluble a-Klotho and Renal Function in Patients with Chronic Kidney Disease: A Review and Meta-Analysis", BioMed Research International, vol. 2018, Article ID 9481475, 12 pages, (Aug. 2018). https://doi.org/10.1155/2018/9481475.
Zhou et al. "Klotho gene deficiency causes salt-sensitive hypertension via monocyte chemotactic protein-1/CC chemokine receptor 2-mediated inflammation" Journal of the American Society of Nephrology : JASN vol. 26,Jan. 1, 2015: 121-32. doi:10.1681/ASN.2013101033.
Zhou et al. "Sonic hedgehog signaling in kidney fibrosis: a master communicator" Science China. Life sciences vol. 59,Sep. 9, 2016: 920-9. doi:10.1007/s11427-016-0020-y.
Zou et al. "The role of klotho in chronic kidney disease." BMC nephrology vol. 19,1 285. Oct. 22, 2018, doi:10.1186/s12882-018-1094-z.
Zununi et al. "Klotho and Renal Fibrosis," Nephro-Urol Mon. (Nov. 2013) 5(5):946-948. doi:10.5812/numonthly.16179.

International Search Report for International Application No. PCT/US2020/021556, dated Jun. 29, 2020, 3 pages.
International Written Opinion for International Application No. PCT/US2020/021556, dated Jun. 29, 2020, 4 pages.
Alves et al. "A mesenchymal stromal cell gene signature for donor age" PLoS One. 2012;7(8):e42908. doi: 10.1371/journal.pone.0042908. Epub Aug. 23, 2012. PMID: 22927939; PMCID: PMC3426516.
Apel et al. (2010), Effect of locally delivered IGF-1 on nerve regeneration during aging: an experimental study in rats, Muscle & nerve, 41(3), 335-341. doi.org/10.1002/mus.21485.
Ayden et al. "Focusing of electromagnetic waves by a left-handed metamaterial flat lens" Optics Express (Oct. 31, 2005) 13(22):8753-8759.
Bäck et al. "Endogenous Calcification Inhibitors in the Prevention of Vascular Calcification: A Consensus Statement From the COST Action EuroSoftCalcNet" Front. Cardiovasc. Med., 918 Jan. 2019): doi.org/10.3389/fcvm.2018.00196.
Bourdillon et al. "Electromagnetic Brain Stimulation in Patients With Disorders of Consciousness" Front. Neurosci., (Mar. 18, 2019): doi.org/10.3389/fnins.2019.00223.
Bowser et al. "Effects of the activin A-myostatin-follistatin system on aging bone and muscle progenitor cells" Exp Gerontol. Feb. 2013;48(2):290-7. doi: 10.1016/j.exger.2012.11.004. Epub Nov. 2, 2012. PMID: 23178301; PMCID: PMC3678732.
Bre et al. "Prevention of bioprosthetic heart valve calcification: strategies and outcomes". Curr Med Chem. 2014;21(22):2553-64. doi: 10.2174/0929867321666131212151216. PMID: 24358975.
Cai et al. "Intermedin inhibits vascular calcification by increasing the level of matrix ?-carboxyglutamic acid protein", Cardiovascular Research, vol. 85, Issue 4, Mar. 1, 2010, pp. 864-873, doi.org/10.1093/cvr/cvp366.
Caradu et al. "Endogenous Sonic Hedgehog limits inflammation and angiogenesis in the ischaemic skeletal muscle of mice". Cardiovasc Res. Apr. 1, 2018;114(5):759-770. doi: 10.1093/cvr/cvy017. PMID: 29365079.
Carboni et al. "An initial study on the effect of functional electrical stimulation in erectile dysfunction: a randomized controlled trial." Int J Impot Res. Jun. 2018; 30(3):97-101. doi: 10.1038/s41443-018-0024-8. Epub May 22, 2018. PMID: 29785045.
Chen et al. "The Strategy to Prevent and Regress the Vascular Calcification in Dialysis Patients", BioMed Research International, vol. 2017, Article ID 9035193, 11 pages, 2017; doi.org/10.1155/2017/9035193.
Chen et al. "Deficiency in the anti-aging gene Klotho promotes aortic valve fibrosis through AMPKa-mediated activation of RUNX2." Aging Cell vol. 15, 5 (2016): 853-60. doi:10.1111/acel.12494.
Chen et al. "Regenerative hair waves in aging mice and extrafollicular modulators Follistatin, Dkk1, and Sfrp4" J Invest Dermatol. Aug. 2014;134(8):2086-2096. doi: 10.1038/jid.2014.139. Epub Mar. 11, 2014. PMID: 24618599; PMCID: PMC4102635.
Chen et al. "The Role and Mechanism of a-Klotho in the Calcification of Rat Aortic Vascular Smooth Muscle Cells." BioMed Research International vol. 2015 (2015): 194362. doi:10.1155/2015/194362.
Cheng et al. "The Role of SDF-1/CXCR4/CXCR7 in Neuronal Regeneration after Cerebral Ischemia." Frontiers in Neuroscience vol. 11 590. Oct. 24, 2017, doi:10.3389/fnins.2017.00590.
Chera et al. "Diabetes recovery by age-dependent conversion of pancreatic d-cells into insulin producers." Nature, 2014; DOI: 10.1038/nature13633.
Chu et al. "Mechanical stretch induces hair regeneration through the alternative activation of macrophages." Nature Communications, 10(1), 1524 (2019). doi.org/10.1038/s41467-019-09402-8.
Deng et al. "Effects of SDF-1/CXCR4 on the Repair of Traumatic Brain Injury in Rats by Mediating Bone Marrow Derived Mesenchymal Stem Cells" Cell Mol Neurobiol. Mar. 2018; 38(2):467-477. doi: 10.1007/s10571-017-0490-4. Epub May 8, 2017. Erratum in: Cell Mol Neurobiol. Apr. 2021;41(3):617-618. PMID: 28484859.
Dërmaku-Sopjani et al. "Klotho-Dependent Role of 1,25(OH)2D3 in the Brain" Neurosignals. Mar. 31, 2021;29(1):14-23. doi: 10.33594/000000352. PMID: 33784444.

(56) References Cited

OTHER PUBLICATIONS

Diaco et al. "Amniotic fluid-derived stem cells as an effective cell source for transplantation therapy in stroke." Brain Circ 2015;1:119-24.

Dote-Montero et al. "Predictors of Sexual Desire and Sexual Function in Sedentary Middle-Aged Adults: The Role of Lean Mass Index and S-Klotho Plasma Levels. The FIT-AGEING Study." J Sex Med. Apr. 2020;17(4):665-677. doi: 10.1016/j.jsxm.2020.01.016. Epub Feb. 20, 2020. PMID: 32089483.

Fukuoka et al. "Hair Regeneration Therapy: Application of Adipose-Derived Stem Cells." Current Stem Cell Research & Therapy vol. 12,7 (2017): 531-534. doi:10.2174/1574888X12666170522114307.

Garcia et al. "1,25(OH)2vitamin D3 stimulates myogenic differentiation by inhibiting cell proliferation and modulating the expression of promyogenic growth factors and myostatin in C2C12 skeletal muscle cells" Endocrinology. Aug. 2011;152(8):2976-86. doi: 10.1210/en.2011-0159. Epub Jun. 14, 2011. PMID: 21673099; PMCID: PMC3138228.

Geribaldi-Doldán et al. "Protein Kinase C: Targets to Regenerate Brain Injuries?" Front. Cell Dev. Biol., Mar. 20, 2019): doi.org/10.3389/fcell.2019.00039.

Ghuman et al. "Biodegradation of ECM hydrogel promotes endogenous brain tissue restoration in a rat model of stroke". Acta Biomater. Oct. 15, 2018;80:66-84. doi: 10.1016/j.actbio.2018.09.020. Epub Sep. 16, 2018. PMID: 30232030; PMCID: PMC6217851.

Guyot et al. "Pancreatic nerve electrostimulation inhibits recent-onset autoimmune diabetes". Nat Biotechnol 37, 1446-1451 (2019): doi.org/10.1038/s41587-019-0295-8.

Hoyer et al. "Electroconvulsive therapy enhances the anti-ageing hormone Klotho in the cerebrospinal fluid of geriatric patients with major depression." Eur Neuropsychopharmacol. Mar. 2018;28(3):428-435. doi: 10.1016/j.euroneuro.2017.12.012. Epub Dec. 20, 2017. PMID: 29274997.

Hu et al. "Renal and extrarenal actions of Klotho." Seminars In Nephrology vol. 33,2 (2013): 118-29. doi:10.1016/j.semnephrol.2012.12.013.

Jayaraj et al. "Neuroinflammation: friend and foe for ischemic stroke". J Neuroinflammation 16, 142 (2019): doi.org/10.1186/s12974-019-1516-2.

Joo et al. "Various Wavelengths of Light-Emitting Diode Light Regulate the Proliferation of Human Dermal Papilla Cells and Hair Follicles via Wnt/ß-Catenin and the Extracellular Signal-Regulated Kinase Pathways." Annals of Dermatology vol. 29,6 (2017): 747-754. doi:10.5021/ad.2017.29.6.747.

Kim et al. "Wnt/ß-catenin and ERK pathway activation: A possible mechanism of photobiomodulation therapy with light-emitting diodes that regulate the proliferation of human outer root sheath cells." Lasers Surg Med. Dec. 2017;49(10):940-947. doi: 10.1002/lsm.22736. Epub Sep. 25, 2017. PMID: 28944964.

Kinney et al. "High intensity focused electromagnetic therapy evaluated by magnetic resonance imaging: Safety and efficacy study of a dual tissue effect based non-invasive abdominal body shaping." Lasers Surg Med. Jan. 2019,51(1):40-46. doi: 10.1002/lsm.23024. Epub Oct. 10, 2018. PMID: 30302767; PMCID: PMC6585690.

Lang et al. "Therapeutic Interference with Vascular Calcification—Lessons From Klotho-Hypomorphic Mice and Beyond" Front. Endocrinol. (May 2018): doi.org/10.3389/fendo.2018.00207.

Lee et al. "Klotho ameliorates diabetic nephropathy via LKB1-AMPK-PGC1a-mediated renal mitochondrial protection" Biochemical and Biophysical Research Communications vol. 534, Jan. 1, 2021, pp. 1040-1046.

Lei "Mechanisms and Reversal Of Elastin Specific Medial Arterial Calcification." (2014). All Dissertations. 1307; tigerprints.clemson.edu/all_dissertations/1307/.

Lei et al. "Efficacy of reversal of aortic calcification by chelating agents." Calcified Tissue International vol. 93,5 (2013): 426-35. doi:10.1007/s00223-013-9780-0.

Leibrock et al. "NH4CI Treatment Prevents Tissue Calcification in Klotho Deficiency" Journal of the American Society of Nephrology, Oct. 2015, 26 (10) 2423-2433.

Leon et al. "Peripheral Elevation of a Klotho Fragment Enhances Brain Function and Resilience in Young, Aging, and a-Synuclein Transgenic Mice" Cell Reports vol. 20, Issue 6, Aug. 6, 2017, pp. 1360-1371.

Li et al. "GDF10 is a signal for axonal sprouting and functional recovery after stroke" Nat Neurosci 2015; Epub Oct. 15, 2015.

Li et al. "Hair Growth Promotion Activity and Its Mechanism of Polygonum multiflorum." Evid Based Complement Alternat Med. 2015;2015:517901. doi: 10.1155/2015/517901. Epub Jul. 30, 2015. PMID: 26294926; PMCID: PMC4534627.

Lim et al. "a-Klotho Expression in Human Tissues." The Journal Of Clinical Endocrinology And Metabolism vol. 100,10 (2015): E1308-18. doi:10.1210/jc.2015-1800.

Lim et al. "Klotho: A Major Shareholder in Vascular Aging Enterprises" Int. J. Mol. Sci. 2019, 20(18), 4637; doi.org/10.3390/ijms20184637.

Liu et al. "Stem cell competition orchestrates skin homeostasis and ageing". Nature 568, 344-350 (2019); doi.org/10.1038/S41586-019-1085-7.

Malyshevskaya et al. "Role of Electrical Activity in Horizontal Axon Growth in the Developing Cortex: A Time-Lapse Study Using Optogenetic Stimulation" PLOS ONE (2013): doi.org/10.1371/journal.pone.0082954.

Martín-González et al. "Soluble a-Klotho in Liver Cirrhosis and Alcoholism, Alcohol and Alcoholism", vol. 54, Issue 3, May 2019, pp. 204-208.

Martín-Núñez et al. "Implications of Klotho in vascular health and disease" World J Cardiol. Dec. 26, 2014; 6(12):1262-1269.

Martinez-Redondo et al. "aKLOTHO and sTGFßR2 treatment counteract the osteoarthritic phenotype developed in a rat model". Protein Cell 11, 219-226 (2020): doi.org/10.1007/s13238-019-00685-7.

Mir et al. "IGF-1 mediated Neurogenesis Involves a Novel RIT1/Akt/Sox2 Cascade." Sci Rep 7, 3283 (2017): doi.org/10.1038/s41598-017-03641-9.

Missoum et al. "Recent Updates on Mesenchymal Stem Cell Based Therapy for Acute Renal Failure" Curr Urol 2019;13:189-199; DOI: 10.1159/000499272.

Morales-García et al. "The alkaloids of Banisteriopsis caapi, the plant source of the Amazonian hallucinogen Ayahuasca, stimulate adult neurogenesis in vitro". Sci Rep 7, 5309 (2017): doi.org/10.1038/s41598-017-05407-9.

Schardong et al. "Intradialytic neuromuscular electrical stimulation reduces DNA damage in chronic kidney failure patients: a randomized controlled trial," (Mar. 2018) Biomarkers, 23:5, 495-501, DOI: 10.1080/1354750X.2018.1452049.

Takenaka et al. "Klotho protein supplementation reduces blood pressure and renal hypertrophy in db/db mice, a model of type 2 diabetes" Acta Physiol (Oxf). Feb. 2019; 225(2):e13190. doi: 10.1111/apha.13190. Epub Oct. 16, 2018.

Zhu et al. "Klotho controls the brain-immune system interface in the choroid plexus" E11388-E11396 PNAS, vol. 115, No. 48, www.pnas.org/cgi/doi/10.1073/pnas.1808609115 accessed Apr. 12, 2019.

Schardong et al. "Effects of Intradialytic Neuromuscular Electrical Stimulation on Strength and Muscle Architecture in Patients With Chronic Kidney Failure: Randomized Clinical Trial." Artif Organs. Nov. 2017;41(11):1049-1058. doi: 10.1111/aor.12886. Epub Jun. 16, 2017. (Abstract Only).

Sanchez-NiNo et al. "Klotho to Treat Kidney Fibrosis" J Am Soc Nephrol 24: 687-689, 2013. doi: 10.1681/ASN.2013030294.

Salcedo et al., "Low current electrical stimulation upregulates cytokine expression in the anal sphincter," Int. J. Colorectal Dis., Feb. 2012;27(2):221-5 doi: 10.1007/s00384-011-1324-3. Epub (Oct. 2011).

Ranjit et al., "Potential neuroprotective role of astroglial exosomes against smoking-induced oxidative stress and HIV-1 replication in the central nervous system," Expert Opin Ther Targets. Aug. 2018; 22(8):703-714.

Prochazka et al., "Cocktail of Factors from Fat-derived Stem Cells Shows Promise for Critical Limb Ischemia" http://www.sciencenewsline.com/news/2016012204520017.html (Jan. 21, 2016).

Hopkins Medicine "Overview of Pacemakers and Implantable Cardioverter Defibrillators (ICDs)," hopkinsmedicine.org/healthlibrary/

(56) References Cited

OTHER PUBLICATIONS conditions/cardiovascular_diseases/overview_of_pacemakers_and_implantable_cardioverter_defibrillators_icds_85,P00234/.
Ferrari "The Effect of Electrical Stimulation on Aged Skeletal Muscle Regenerative Potential" http://d-scholarship.pitt.edu/28094/1/FerrariRJ_ETD_May_31_2016_PDF.pdf.
Fatemi et al., "Imaging elastic properties of biological tissues by low-frequency harmonic vibration" Proceedings of the IEEE, 91(10):1503-1519 (Oct. 2003).
DiIorio "High-frequency external muscle stimulation in acute kidney injury (AKI): potential shortening of its clinical course" Clinical Nephrology, vol. 78—No. Suppl. Jan. 2012 (S37-S45).
Dalise et al., "Biological effects of dosing aerobic exercise and neuromuscular electrical stimulation in rats", Sci Rep. Sep. 7, 2017; 7(1):10830.
Columbia "Implant Procedure Concepts—Pacemaker, ICD and CRT Overview," columbia.edu/itc/hs/medical/hickey/docs/Pacemaker,%20ICD%20and%20CRT%20Overview%20022007.pdf.
Chernet "Transmembrane voltage potential is an essential cellular parameter for the detection and control of tumor development in a Xenopus model," Dis. Models & Mech. 6, pp. 595-607 (2013); doi:10.1242/dmm.010835.
Bruggemann et al. "Effects of Neuromuscular Electrical Stimulation During Hemodialysis on Peripheral Muscle Strength and Exercise Capacity: A Randomized Clinical Trial." Arch Phys Med Rehabil. May 2017;98(5):822-831.e1. doi: 10.1016/j.apmr.2016.12.009. Epub Jan. 16, 2017. (Abstract Only).
Brooks et al., "Bioelectric impedance predicts total body water, blood pressure, and heart rate during hemodialysis in children and adolescents" J. Ren Nutr., 18(3):304-311 (May 2008); doi: 10.1053/j.jrn.2007.11.008.
Nakamura et al. "Eicosapentaenoic acid prevents arterial calcification in klotho mutant mice." PLoS One. Aug. 3, 2017;12(8):e0181009. doi: 10.1371/journal.pone.0181009. PMID: 28771600; PMCID: PMC5542469.
Negaresh et al. "The effect of resistance training on quadriceps muscle volume and some growth factors in elderly and young men" Adv Gerontol. 2017;30(6):880-887. PMID: 29608833.
Nih et al. "Dual-function injectable angiogenic biomaterial for the repair of brain tissue following stroke". Nature Mater 17, 642-651 (2018): doi.org/10.1038/s41563-018-0083-8.
Noguchi et al. "Alteration of skin wound healing in keratinocyte-specific mediator complex subunit 1 null mice" PLoS One. Aug. 14, 2014;9(8):e102271. doi: 10.1371/journal.pone.0102271. PMID: 25122137; PMCID: PMC4133190.
Nowak et al. "Prognostic Value and Link to Atrial Fibrillation of Soluble Klotho and FGF23 in Hemodialysis Patients" PLoS One. Jul. 3, 2014;9(7):e100688. doi: 10.1371/journal pone.0100688.
O'Neill et al. "Recent progress in the treatment of vascular calcification." Kidney International vol. 78,12 (2010): 1232-9. doi:10.1038/ki.2010.334.
Pai et al. "Endogenous Gradients of Resting Potential Instructively Pattern Embryonic Neural Tissue via Notch Signaling and Regulation of Proliferation." Journal of Neuroscience, 2015; 35 (10): 4366 DOI: 10.1523/JNEUROSCI.1877-14.2015.
Papaioannou et al. "Sonic Hedgehog signaling limits atopic dermatitis via Gli2-driven immune regulation" J Clin Invest. 2019; 129(8):3153-3170; doi.org/10.1172/JCI125170.
Paroni et al. "Klotho Gene and Selective Serotonin Reuptake Inhibitors: Response to Treatment in Late-Life Major Depressive Disorder". Mol Neurobiol. Mar. 2017;54(2):1340-1351. doi: 10.1007/s12035-016-9711-y. Epub Feb. 3, 2016. PMID: 26843110.
Prather et al. "Longevity factor klotho and chronic psychological stress". Translational Psychiatry, 2015; 5 (6): e585 DOI: 10.1038/tp.2015.81.
Prud'Homme et al. "The anti-aging protein Klotho is induced by GABA therapy and exerts protective and stimulatory effects on pancreatic beta cells." Biochem Biophys Res Commun. Dec. 2, 2017;493(4):1542-1547. doi: 10.1016/j.bbrc.2017.10.029. Epub Oct. 6, 2017. PMID: 28993191.
Qi et al. "Enhancement of neural stem cell survival, proliferation and differentiation by IGF-1 delivery in graphene oxide-incorporated PLGA electrospun nanofibrous mats" RSC Adv., 2019,9, 8315-8325.
Rhee et al. "Neural stem cells secrete factors facilitating brain regeneration upon constitutive Raf-Erk activation." Sci Rep 6, 32025 (2016): doi.org/10.1038/srep32025.
Sachdeva et al. "Klotho and the Treatment of Human Malignancies" Cancers 2020, 12, 1665; doi:10.3390/cancers12061665.
Sadagurski et al. "Insulin-like growth factor 1 receptor signaling regulates skin development and inhibits skin keratinocyte differentiation." Molecular and Cellular Biology vol. 26,7 (2006): 2675-87. doi:10.1128/MCB.26.7.2675-2687.2006.
Savastano et al. "Insulin-like Growth Factor-1, Psoriasis, and Inflammation: A Ménage à Trois?" European Journal of Inflammation vol. 9 issue: 3, pp. 277-283 (2011).
Sharma et al. "Insulin demand regulates ß cell number via the unfolded protein response." Journal of Clinical Investigation, 2015; DOI: 10.1172/JCI79264.
Sieg "Mini-review of neural regeneration peptides in brain development." Journal of Stem Cell Research & Therapeutics 1 (2016): DOI: 10.15406/JSRT.2016.01.00025 Corpus ID: 14566389.
Sood et al. "Fetal Brain Extracellular Matrix Boosts Neuronal Network Formation in 3D Bioengineered Model of Cortical Brain Tissue" ACS Biomater. Sci. Eng. 2016, 2, 1, 131-140.
Stief et al. "Functional electromyostimulation of the corpus cavernosum penis—preliminary results of a novel therapeutic option for erectile dysfunction," World J. Urol. (1995) 13:243-247.
Sun et al. "Overexpression of Klotho suppresses liver cancer progression and induces cell apoptosis by negatively regulating wnt/ß-catenin signaling pathway." World Journal of Surgical Oncology vol. 13 307. Oct. 24, 2015, doi:10.1186/S12957-015-0717-0.
Tang-Schomer MD. "3D axon growth by exogenous electrical stimulus and soluble factors." Brain Res. Jan. 1, 2018;1678:288-296. doi: 10.1016/j.brainres.2017.10.032. Epub Oct. 31, 2017. PMID: 29097106.
The et al. "Mechanistic Roles of Matrilin-2 and Klotho in Modulating the Inflammatory Activity of Human Aortic Valve Cells" Cells 2020, 9, 385; doi:10.3390/cells9020385.
Thurston et al. "Tumor necrosis factor and interferon-gamma down-regulate Klotho in mice with colitis". Gastroenterology. Apr. 2010;138(4):1384-94, 1394.e1-2. doi: 10.1053/j.gastro.2009.12.002. Epub Dec. 11, 2009. PMID: 20004202; PMCID: PMC3454518.
Torbus-Paluszczak et al. "Klotho protein in neurodegenerative disorders," Neurol. Sci. 39, 1677-1682 (2018): doi.org/10.1007/s10072-018-3496-x.
Van Kampen et al. "Treatment of Erectile Dysfunction by Perineal Exercise, Electromyographic Biofeedback, and Electrical Stimulation," Phys. Ther. 2003; 83(6):536-543.
Wang, et al. "Secreted klotho from exosomes alleviates inflammation and apoptosis in acute pancreatitis." American Journal Of Translational Research vol. 11,6 3375-3383. Jun. 15, 2019.
Witkowski et al. "Klotho—a Common Link in Physiological and Rheumatoid Arthritis-Related Aging of Human CD4+ Lymphocytes" J Immunol (2007), 178(2):771-777; DOI: doi.org/10.4049/jimmunol.178.2.771.
Xia et al. "Klotho Contributes to Pravastatin Effect on Suppressing IL-6 Production in Endothelial Cells." Mediators of Inflammation vol. 2016 (2016): 2193210. doi:10.1155/2016/2193210.
Xie et al. "Klotho Acts as a Tumor Suppressor in Cancers" Jul. 2013 Pathology & Oncology Research 19(4) DOI:10.1007/s12253-013-9663-8.
Xuan et al. "Changes in expression of klotho affect physiological processes, diseases, and cancer." Iranian journal of basic medical sciences vol. 21,1 (2018): 3-8.
Yaden et al. "Follistatin: a novel therapeutic for the improvement of muscle regeneration," Journal of Pharmacology and Experimental Therapeutics Mar. 13, 2014, jpet.113.211169; DOI: doi.org/10.1124/jpet.113.211169.
Yamauchi et al. "Wound healing delays in a—Klotho-deficient mice that have skin appearance similar to that in aged humans—Study of

(56) References Cited

OTHER PUBLICATIONS delayed wound healing mechanism" Biochemical and Biophysical Research Communications vol. 473, Issue 4, May 13, 2016, pp. 845-852.

Yarbrough et al. "Specific binding and mineralization of calcified surfaces by small peptides." Calcified Tissue International vol. 86,1 (2010): 58-66. doi:10.1007/s00223-009-9312-0.

Zhang et al. "Association of Klotho and interleukin 6 gene polymorphisms with aging in Han Chinese population." J Nutr Health Aging. Dec. 2014;18(10):900-4. doi: 10.1007/s12603-014-0470-z. PMID: 25470806.

Zhang et al. "Klotho Protein Protects Human Keratinocytes from UVB-Induced Damage Possibly by Reducing Expression and Nuclear Translocation of NF-?B." Medical Science Monitor: International Medical Journal of Experimental and Clinical Research vol. 24 8583-8591. Nov. 27, 2018, doi:10.12659/MSM.910687.

Zhao et al. "Enhancing endogenous capacity to repair a stroke-damaged brain: An evolving field for stroke research" Progress in Neurobiology vols. 163-164, Apr.-May 2018, pp. 5-26.

Zhou et al. "Advance of Stem Cell Treatment for Traumatic Brain Injury" Front. Cell. Neurosci., (Aug. 13, 2019): doi.org/10.3389/fncel.2019.00301.

Ziaaldini et al. "Exercise training increases anabolic and attenuates catabolic and apoptotic processes in aged skeletal muscle of male rats" Exp Gerontol. Jul. 2015; 67:9-14. doi: 10.1016/j.exger.2015.04.008. Epub Apr. 21, 2015. PMID: 25910622.

Nodzo et al., "Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), 1668-1675.

Nordstorm "Electrical Stimulation Blood Pressure Treatment Devices Market to Set Astonishing Growth by 2026" Art. Apr. 4, 2019 Gator Ledger.

Norton et al. "Bioelectric Perturbations of Bone: Research Directions and Clinical Applications" Angle Orthod (1984) 54 (1): 73-87.

Novickij et al., "Induction of Different Sensitization Patterns of MRSA to Antibiotics Using Electroporation," Molecules, vol. 23, (2018), Article 1799, 10 pages.

Odell et al. "Anti-inflammatory Effects of Electronic Signal Treatment" Pain physician. 11. 891-907 (2008). 10.36076/ppj.2008/11/891.

Payne et al. "Bioelectric Control of Metastasis in Solid Tumors" Bioelectricityvol. 1, No. 3, (Sep. 16, 2019) https://doi.org/10.1089/bioe.2019.0013.

Pozo et al., "Bioelectric Effect and Bacterial Biofilms. A Systematic Review," The International Journal of Artificial Organs, vol. 31, (2008), pp. 786-795.

Pozo et al., "Effect of Electrical Current on the Activities of Antimicrobial Agents Against Pseudomonas Aeruginosa, *Staphylococcus aureus*, and *Staphylococcus epidermidis* Biofilms," Antimicrobial Agents and Chemotherapy, vol. 53, (2009), pp. 35^0.

Pozo et al., "Prevention of *Staphylococcus epidermidis* Biofilm Formation Using Electrical Current," Journal of Applied Biomaterials & Functional Materials, vol. 12, (2014), pp. 81-83.

Pozo et al., "The Electricidal Effect: Reduction of *Staphylococcus* and Pseudomonas Biofilms by Prolonged Exposure to Low-Intensity Electrical Current," Antimicrobial Agents and Chemotherapy, vol. 53, (2009), pp. 41-45.

Pupo et al., Electrotherapy on Cancer: Experiment and Mathematical Modeling, Current Cancer Treatment—Novel Beyond Conventional Approaches, Prof. Oner Ozdemir (Ed.) ISBN: 978-953-307-397-2, InTech, Available from: http://www.intechopen.com/books/current-cancer-treatment-novel-beyond-conventional-approaches/electrotherapy-on-cancer-experiment-and-mathematical-modeling, 2011.

Puro et al "Bioelectric impact of pathological angiogenesis on vascular function," PNAS Aug. 30, 2016 113 (35) 9934-9939; published ahead of print Aug. 22, 2016 https://doi.org/10.1073/pnas.1604757113.

Roy et al., "Disposable Patterned Electroceutical Dressing (PED-10) Is Safe for Treatment of Open Clinical Chronic Wounds," Advances in Wound Care, vol. 8, (1019), pp. 149-159.

Sabbah "Electrical vagus nerve stimulation for the treatment of chronic heart failure", Cleve Clin J Med, 78 Suppl 1: S24-9. doi: 10.3949/ccjm.78.s1.04 (Aug. 2011).

Sabino-Carvalho et al., "Non-invasive Vagus Nerve Stimulation Acutely Improves Blood Pressure Control in a Placebo Controlled Study," The FASEB Journal, vol. 31, 2017, available online at < https://www.fasebj.org/doi/abs/10.1096/fasebj.31.1_supplement.848.8 >, 2 pages) Abstract Only.

Sahmeddini et al., "Electro-Acupuncture Stimulation at Acupoints Reduced the Severity of Hypotension During Anesthesia in Patients Undergoing Liver Transplantation," Journal of Acupuncture and Meridian Studies, vol. 5, Issue 1, (2012), pp. 11-14.

Sandvik et al., "Direct Electric Current Treatment under Physiologic Saline Conditions Kills *Staphylococcus epidermidis* Biofilms via Electrolytic Generation of Hypochlorous Acid," PloS one, vol. 8, (Feb. 2013), e55118, 14 pages.

Santos et al. "Interferential electrical stimulation improves peripheral vasodilatation in healthy individuals" Braz J Phys Ther. May-Jun. 2013; 17(3):281-288.

Sartori et al. "Effects of Transcutaneous Electrical Nerve Stimulation in Autonomic Nervous System of Hypertensive Patients: A Randomized Controlled Trial" Current Hypertension Reviews, Apr. 2018, 14, 66-71.

Schardong et al., "Intradialytic neuromuscular electrical stimulation reduces DNA damage in chronic kidney failure patients: a randomized controlled trial," Biomarkers, vol. 23, Issue 5, 2018, pp. 1-11.

Schmidt-Malan et al., "Activity of Fixed Direct Electrical Current in Experimental *Staphylococcus aureus* Foreign-Body Osteomyelitis," Diagnostic Microbiology and Infectious Disease, vol. 93, (2019), pp. 92-95.

Shirtliff et al., "Assessment of the Ability of the Bioelectric Effect to Eliminate Mixed-Species Biofilms," Applied and Environmental Microbiology, vol. 71, (2005), pp. 6379-6382.

Showkatbakhsh et al. "Effect of Intra-Canal Direct Current Electric Stimulation on Orthodontic Tooth Movement: An Experimental Study in Canines" Journal of Dental School 2016; 34(3): 157-67.

Showkatbakhsh et al. "The effect of pulsed electromagnetic fields on the acceleration of tooth movement." World J Orthod. 2010 Winter;11(4):e52-6.

Silvers et al. "The Bioelectric Code: Reprogramming Cancer and Aging from the Interface of Mechanical and Chemical Microenvironments," Front. Cell Dev. Biol., Mar. 6, 2018; doi.org/10.3389/fcell.2018.00021.

Spadari et al., Electrical stimulation enhances tissue reorganization during orthodontic tooth movement in rats; Clinical Oral Investigations, Jan. 2017, vol. 21, Issue 1, pp. 111-120, Abstract.

Spiridonov et al. "Effect of Transcutaneous Electrical Stimulation of Nerves on Blood Pressure and Blood Content of Neuropeptide CGRP and Nitric Oxide in Hypertensive Rats with Metabolic Disturbances" Bull Exp Biol Med (Feb. 2019) 166: 436-437.

Stein et al., "The effect of transcutaneous electrical nerve stimulation on blood pressure," Blood Pressure, vol. 22, Issue 3, 2013, available online at < https://www.tandfonline.com/doi/full/10.3109/08037051.2012.722271 >, 5 pages.

Stoodley b I al., "Influence of Electric Fields and pH on Biofilm Structure as Related to the Bioelectric Effect," Antimicrobial Agents and Chemotherapy, vol. 41, (1997), pp. 1876-1879.

Su et al. "Klotho protein lowered in elderly hypertension" Int J Clin Exp Med (Aug. 2014) 7(8):2347-2350.

Sultana et al., "Electrochemical Biofilm Control: A Review," Biofouling, vol. 31, (2015), pp. 745-758.

Sun "Regulation of Blood Pressure by Klotho" University of Oklahoma Health Sciences Center, Oklahoma City, OK, United States; accessed Jun. 2, 2021; https://grantome.com/grant/NIH/R01-HL102074-01A1.

Sutherland et al. "Prolonged electrical stimulation of the nipples evokes intermittent milk ejection in the anaesthetised lactating rat," Exp Brain Res. 1987;66(1):29-34.

(56) References Cited

OTHER PUBLICATIONS

Szkotak et al., "Differential Gene Expression to Investigate the Effects of Low-Level Electrochemical Currents on Bacillus subtilis," AMB Express, vol. 1, (Nov. 2011), 12 pages.
Takenaka et al. "Klotho Supplementation AttenuatesBlood Pressure and Cyst Growth InMouse Polycystic Kidney Disease" Journal of Hypertension: vol. 36—Issue—p. e76 (Jun. 2018).
Tyler "Nature's Electric Potential: A Systematic Review of the Role of Bioelectricity in Wound Healing and Regenerative Processes in Animals, Humans, and Plants" Front. Physiol., (Sep. 2017) https://doi.org/10.3389/fphys.2017.00627.
Ucirvine, "Electroacupuncture for Hypertension in Women: The Susan Samueli Center for Integrative Medicine at UC Irvine is Recruiting Patients for a Study", Principle Investigators: Dr. Stephanie Tjen-a-Looi and Dr. Shaista Malik, MOD# 20266, HS# 1999-2222, (2017), 1 page.
Van Dam et al. "RANK/RANKL signaling inhibition may improve the effectiveness of checkpoint blockade in cancer treatment" Critical Reviews in Oncology/Hematology vol. 133, Jan. 2019, pp. 85-91.
Vilela-Martin et al., "Effects of Transcutaneous Electrical Nerve Stimulation (TENS) on Arterial Stiffness and Blood Pressure in Resistant Hypertensive Individuals: Study Protocol for a Randomized Controlled Trial," Trials, vol. 17, (2016), pp. 1-13.
Zalavras, Charalampos G. "CORR Insights(Registered): Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), pp. 1676-1678.
Zaniboni et al. "Do electrical current and laser therapies improve bone remodeling during an orthodontic treatment with corticotomy?" Clin Oral Invest 23, 4083-4097 (2019). https://doi.org/10.1007/s00784-019-02845-9.
Zhou et al. "Klotho Ameliorates Kidney Injury and Fibrosis and Normalizes Blood Pressure by Targeting the Renin-Angiotensin System" The American Journal of Pathology, vol. 185, No. 12, Dec. 2015.
Zhou et al. "Klotho Gene Deficiency Causes Salt-Sensitive Hypertension via Monocyte Chemotactic Protein-1/CC Chemokine Receptor 2-Mediated inflammation" J Am Soc Nephrol 26: 121-132, 2015 (Accepted Apr. 2014).
Zimmerman et al. "Cancer cell proliferation is inhibited by specific modulation frequencies" Br J Cancer. Jan. 17, 2012;106(2):307-13. doi: 10.1038/bjc.2011.523. Epub Dec. 1, 2011. PMID: 22134506; PMCID: PMC3261663.
Zimmerman et al. "Targeted treatment of cancer with radiofrequency electromagnetic fields amplitude-modulated at tumor-specific frequencies" Chin J Cancer. Nov. 2013;32(11):573-81. doi: 10.5732/cjc.013.10177. PMID: 24206915; PMCID: PMC3845545.
"Electric Tumor Treatment Fields," No. 0827 Policy, aetna.com/cpb/medical/data/800_899/0827.html (Nov. 18, 2016), last visited Sep. 12, 2018.
"Electrical brain stimulation could support stroke recovery," sciencedaily.com/releases/2016/03/160316151108.htm (Mar. 16, 2016), last visited Sep. 12, 2018.
"FDA Approves Algovita Spinal Cord Stimulation System from Greatbatch," http://www.odtmag.com/contents/view_breaking-news/2015-12-02/fda-approves-algovita-spinal-cord-stimulation-jystem-from-greatbatch (Dec. 2, 2015).
Abdel-Rehim "Change of serum klotho protein and its relationship with endothelial dysfunction, oxidative stress and arterial aging in essential hypertensive patients" J Kidney 2018, vol. 4 (Dec. 2018).
Ahrens et al. "Klotho expression is a prerequisite for proper muscle stem cell function and regeneration of skeletal muscle" Ahrens et al. Skeletal Muscle (Jul. 2018) 8:20 pp. 1-14.
Andersson et al. "Drinking, antidiuresis and milk ejection from electrical stimulation within the hypothalamus of the goat," Acta Physiol Scand. Dec. 31, 1955; 35(2):191-201; DOI: 10.1111/j.1748-1716.1955.tb01277.x.
Banerjee, P. "Electrical muscle stimulation for chronic heart failure: an alternative tool for exercise training?" Curr Heart Fail Rep., 7(2):52-8. doi: 10.1007/s11897-010-0013-9 (Jun. 2010).
Barbault et al., Amplitude-modulated electromagnetic fields for the treatment of cancer: Discovery of tumor-specific frequencies and assessment of a novel therapeutic approach, Journal of Experimental & Clinical Cancer Research, Apr. 14, 2009, vol. 28, No. 51, doi:10.1186/1756-9966-28-51, 10 pages.
Barnhill "It's Electric! All About Microcurrent Facials" accessed Aug. 4, 2021, https://intothegloss.com/2016/04/microcurrent-treatment/.
Borgobello, B. "FDA approves the treatment of brain tumors with electrical fields," New Atlas, http://newatlas.com/treatment-of-brain-tumors-with-electrical-fields/21433/(Feb. 13, 2012), last visited Sep. 12, 2018.
Carboni Ei Al. "An initial study on the effect of functional electrical stimulation in erectile dysfunction: a randomized controlled trial" IJIR: Your Sexual Medicine Journal (May 2018) 30:97-101.
Cervera "The interplay between genetic and bioelectrical signaling permits a spatial regionalisation of membrane potentials in model multicellular ensembles," Nature, Scientific Reports, Oct. 12, 2016 vol. 6, Article No. 35201 (2016).
Chang et al. "Pulsed electromagnetic fields stimulation affects osteoclast formation by modulation of osteoprotegerin, RANK ligand and macrophage colony-stimulating factor", Journal of Orthopaedic Research, 23 (2005) 1308-1314.
Chang et al. Effect of Pulse-Burst Electromagnetic Field Stimulation on Osteoblast Cell Activities; Bioelectromagnetics 25:457-465 (2004).
Chemet & Levin, "Transmembrane voltage potential is an essential cellular parameter for the detection and control of tumor development in a Xenopus model," Dis. Models & Mech. 6, pp. 595-607 (2013); doi:10.1242/dmm.010835.
Chen et al. "Secreted Klotho Attenuates Inflammation-Associated Aortic Valve Fibrosis in Senescence-Accelerated Mice P1" Hypertension. 2018;71:877-885. DOI: 10.1161/HYPERTENSIONAHA. 117.10560.) Downloaded from http://ahajournals.org by on Apr. 24, 2020 (9 pages).
Chen et al. "Nanosecond Pulsed Electric Field (nsPEF) Ablation as an Alternative or Adjunct to Surgery for Treatment of Cancer" Chen et al., Surgery Curr Res 2013, S12 DOI: 10.4172/2161-1076.S12-005.
Chen et al., "Deficiency in the Anti-Aging Gene Klotho Promotes Aortic Valve Fibrosis Through AMPK(Alpha)-Mediated Activation of RUNX2," Aging Cell, vol. 15, (Oct. 2016), pp. 853-860.
Chen et al., "The Role and Mechanism of (Alpha)-Klotho in the Calcification of Rat Aortic Vascular Smooth Muscle Cells," BioMed Research International, vol. 2015, (2015), 7 pages.
Ciria et al., Antitumor effectiveness of different amounts of electrical charge in Ehrlich and fibrosarcoma Sa-37 tumors, BMC Cancer, Nov. 26, 2004, 10 pages, vol. 4, No. 87.
Costa et al. "Treatment of advanced hepatocellular carcinoma with very low levels of amplitude-modulated electromagnetic fields" Br J Cancer. Aug. 23, 2011;105(5):640-8. doi: 10.1038/bjc.2011.292. Epub Aug. 9, 2011. PMID: 21829195; PMCID: PMC3188936.
Costerton et al., "Mechanism of Electrical Enhancement of Efficacy of Antibiotics in Killing Biofilm Bacteria," Antimicrobial Agents and Chemotherapy, vol. 38, (1994), pp. 2803-2809.
Cross El Al. "Milk Ejection following Electrical Stimulation of the Pituitary Stalk in Rabbits," Nature 166, 994-995 (Dec. 9, 1950); doi:10.1038/166994b0 (Abstract Only).
Dai El Al. "Nanosecond Pulsed Electric Fields Enhance the Antitumour Effects of the mTOR Inhibitor Everolimus against Melanoma," Scientific Reports vol. 7, Article No. 39597 (2017).
Fonseca et al. "Electrical stimulation: Complementary therapy to improve the performance of grafts in bone defects?" Journal of Biomedical Materials Research Part B: Applied Biomaterials 2018 vol. 000b, Issue 0.
Froughreyhani et al. "Effect of Electric Currents on Antibacterial Effect of Chlorhexidine Against Entrococcus Faecalis Biofilm: An in Vitro Study," Journal of Clinical and Experimental Dentistry, vol. 10, (Dec. 2018), pp. e1223-e1229.

(56) References Cited

OTHER PUBLICATIONS

Fujiya et al. "Microcurrent Electrical Neuromuscular Stimulation Facilitates Regeneration of Injured Skeletal Muscle in Mice" Journal of Sports Science and Medicine (Jun. 2015) 14, 297-303.

Giladi et al., "Microbial Growth Inhibition by Alternating Electric Fields," Antimicrobial Agents and Chemotherapy, vol. 52, (2008), pp. 3517-3522.

Golberg et al., "Pulsed Electric Fields For Burn Wound Disinfection in a Murine Model," Journal of Burn Care & Research, vol. 36, (2015), pp. 7-13.

Grad, D., "Electrical Scalp Device Can Slow Progression of Deadly Brain Tumors", New York Times, https://www.nytimes.com/2014/11/16/health/electrical-scalp-device-can-slow-progression-of-deadly-brain-tumors.html?r=0(Nov. 15, 2014).

Hu et al. "Klotho Deficiency Causes Vascular Calcification in Chronic Kidney Disease" J Am Soc Nephrol. Jan. 2011; 22(1): 124-136.

Hunckler et al. "A current affair: electrotherapy in wound healing" Journal of Multidisciplinary Healthcare (Apr. 2017)10 179-194.

Israeli innovation uses nerve stimulation to treat heart failure https://www.israel21c.org/israeli-innovation-uses-nerve-stimulation-to-treat-heart-failure/ (Feb. 11, 2007).

Jamal et al. "Klotho, Hypertension and Arterial Stiffness: A Review" Austin J Nephrol Hypertens.(Jul. 2019) 6(2): 1082.

Jansen et al. "Stimulation of osteogenic differentiation in human osteoprogenitor cells by pulsed electromagnetic fields: an in vitro study" BMC Musculoskelelal Disorders (2010) 11:188 DOI: 10.1186/1471-2474-11-188.

JCCR "Emerging roles of klotho in cardiovascular diseases%5D" Accessed Jun. 2, 2021 https://medcraveonline.com/JCCR/emerging-roles-of-klotho-in-cardiovascular-diseases.html%5D.

Jing-Hong et al. "Electrochemical Therapy of Tumors" Hindawi Publishing Corporation, Conference Papers in Medicine, vol. 2013, Article ID 858319, 13 pages, http://dx.doi.org/10.1155/2013/858319.

Kim et al., The effects of electrical current from a micro-electrical device on tooth movement, Korean Drthod., Oct. 2008, 38(5):337-346, Abstract submitted in English.

Lasserre et al., "Influence of Low Direct Electric Currents and Chlorhexidine Upon Human Dental Biofilms," Clinical and Experimental Dental Research, vol. 2, (Jul. 2016), pp. 146-154.

Leibrock et al:, "NH4CI Treatment Prevents Tissue Calcification in Klotho Deficiency," Journal of the American Society of Nephrology, vol. 26, (2015), pp. 2423-2433.

Leonhardt "Micro Stimúlator" http://www.bioleonhardt.com/micro-stimulator/.

Leonhardt "PressureStim Receives IRB Approval to Launch Bioelectric Hypertension Treatment Clinical Study" Accessed Jun. 2, 2021, https://www.prdistribution.com/news/pressurestim-receives-irb-approval-to-launch-bioelectric-hypertension-treatment-clinical-study-2.html?fbclid=IwAR28Dh97RAKXXHrfgUONKW1pk-MWyeF_ibUIpQc_2XEN32C6sS%E2%80%A6.

Li et al., "Long-Lasting Reduction of Blood Pressure by Electroacupuncture in Patients with Hypertension: Randomized Controlled Trial," Medical Acupuncture, vol. 27, No. 4, (2015), pp. 253-266.

Malakhov et al. "Assessment of Efficacy of Non-Invasive Peripheral Transcutaneous Electrical Nerve Stimulation for Correction of Blood Pressure in Patients With Arterial Hypertension" Journal of Hypertension: Jul. 2019—vol. 37—Issue—p e88-e89 doi: 10.1097/01.hjh.0000570296.70620.44.

Maltese et al. "The Putative Role of the Antiageing Protein Klotho in Cardiovascular and Renal Disease" Hindawi Publishing Corporation International Journal of Hypertension, (Sep. 2011) vol. 2012, Article ID 757469, 5 pages.

Metro News "Bioelectricity: A shocking revolution in skincare?" Website accessed Aug. 4, 2021 https://metro.co.uk/2010/09/26/bioelectricity-a-shocking-revolution-in-skincare-523763/.

Moe, "Klotho: A Master Regulator of Cardiovascular Disease?," Circulation, vol. 125, (2012), pp. 2181-2183.

Muratori et al. "The cytotoxic synergy of nanosecond electric pulses and low temperature leads to apoptosis" Sci Rep 6, 36835 (2016). https://doi.org/10.1038/srep36835.

Nodzo et al., "Cathodic Electrical Stimulation Combined With Vancomycin Enhances Treatment of Methicillin-Resistant *Staphylococcus aureus* Implant-Associated Infections," Clinical Orthopaedics and Related Research, vol. 473, (2015), pp. 2856-2864.

\* cited by examiner

Follistatin: 10V, 50Hz, Square wave

IGF-1: 3.0mV, 22Hz, square wave

PDGF30%: 3V/cm (100mV here), 10Hz, pulse width 200us, square wave

PDGF230%: 20V/cm (7.0V here), 100Hz, pulse width 100us, square wave

Proliferation: 15mV, 70Hz, square wave

Proliferation: 2.5-6.0V (4V here), 20Hz, pulse width 200-700us, square wave

SDF-1: 3.5mV, 30Hz, square wave

SDF-1 (2nd part): 0.25mA (3.0V shown here), 100Hz, 100us pulse width, square wave Tropoelastin: 60mV, 50Hz, square wave

| KLOTHO | | OPG | KLOTHO |
|---|---|---|---|
| 0.649913 | | 21.31382 | 2.480879 |
| 496.0868 | | 3.083639 | 1.109483 |
| 1.946573 | | | |
| | | | |
| 3.416525 | | | |
| 1.736225 | | | |
| 4.655161 | | | |
| | | | |
| | | | |
| KLOTHO | | | |
| 0.649913 | | 11.02667 | |
| 1.946573 | | 17.3098 | |
| 3.416525 | | 25.70403 | |
| 1.736225 | | 26.38801 | |
| 4.655161 | | 26.14059 | |
| 2.480879 | | 21.31382 | |
| 1.564877 | | 6.895227 | |
| 0.699834 | | 3.083639 | |

FIG. 14

KLOTHO MODULATION

FIELD

The application relates generally to the field of medical devices and associated treatments, and more specifically to precise bioelectrical stimulation of a subject's tissue, possibly augmented with the administration of a composition comprising, among other things, stem cells and nutrients, useful to stimulate and treat the subject, the subject's tissue(s), the subject's organ(s), and/or the subject's cells. More specifically, the application relates to a device, programmed bioelectric signaling sequences, and associated methods for the controlled expression of Klotho via precise bioelectrical signaling sequences.

BACKGROUND

Klotho protein is a kidney-secreted hormone that is known to be both membrane-bound and secreted. In man, Klotho is associated with muscle regeneration, rejuvenation, and neural protection. Loss of Klotho contributes to the aging-like features of human chronic kidney disease ("CKD") and progression of CKD. Its deficiency is also associated with degenerative processes and accelerated aging.

As found by S. Ranjit et al., "Since Klotho cannot cross the blood brain barrier, it is speculated that there exist two different pools of Klotho, one secreted from kidney into serum and other secreted by the choroid plexus into cerebrospinal fluid. Due to these reasons, therapeutic use of Klotho to provide neuroprotection [to reduce neuroinflammation and oxidative damage] is limited". S. Ranjit et al. "Potential neuroprotective role of astroglial exosomes against smoking-induced oxidative stress and HIV-1 replication in the central nervous system." *Expert Opin Ther Targets*. 2018 August; 22(8):703-714.

Ricardo Ferrari described that the enhanced regenerative response in aged muscle following two weeks of electrical stimulation "Estim" (i.e., a Neuromuscular Stimulator (Empi 300 PV, St Paul, Minn., US)) was associated with a somewhat limited, but still increased expression of Klotho (similar to that achieved from muscle contraction, e.g., exercise). Ricardo Ferrari "The Effect of Electrical Stimulation on Aged Skeletal Muscle Regenerative Potential" d-scholarship.pitt.edu/28094/1/FerrariRJ_ETD_May_31_2016_PDF.pdf.

Ferrari also observed a direct relationship between Klotho expression and the percentage of senescent muscle precursor cells ("MPCs"). When Klotho was inhibited through siRNA in young MPCs and aged MPCs exposed to an Estim protocol, Ferrari observed a significantly increased percentage of senescence cells. Such findings suggest that Klotho is inversely associated with senescence cells, and that Estim modulates Klotho expression in aged MPCs, and there is precedent to suggest that Klotho plays a role in inhibiting cellular senescence. See also, Dalise et al. "Biological effects of dosing aerobic exercise and neuromuscular electrical stimulation in rats", *Sci Rep.* 2017 September 7; 7(1):10830.

Using the skin and small intestine as models, others have demonstrated that Klotho enhances stem cell regenerative potential and promotes tissue healing through an inhibition of Wnt signaling activation. Recent studies demonstrated that Klotho is able to directly bind to Wnt ligands extracellularly, thereby inhibiting renal fibrosis formation.

BRIEF SUMMARY

Described herein is a bioelectric stimulator particularly configured to activate expression and/or release of Klotho in cellular tissue. In certain embodiments, the bioelectric stimulator is further configured to activate expression and/.or release of stromal cell-derived factor 1 ("SDF-1"), insulin-like growth factor 1 ("IGF-1"), platelet-derived growth factor ("PDGF"), follistatin, tropoelastin, and any combination thereof.

Also described is a bioelectric stimulator including: a power source (e.g., battery, capacitor, or other suitable source of electricity), and means for delivering an electrical signal to a subject's tissue (e.g., via electrode(s) or wirelessly). The bioelectric stimulator utilizes the electrical signal to precisely control protein expression in the tissue on demand.

In certain cases, the bioelectric stimulator is programmed to produce a bioelectric signal that stimulates target tissue to express and/or release Klotho polypeptide by the target tissue by utilizing a bioelectric signal comprising a biphasic square pulse at 20 Hz, 0.1 V (100 mV), and a 7.8 ms pulse duration for 24 hours of stimulation.

The amount of Klotho expression enhanced by the herein described system is greater than that seen with muscle stimulation or muscle contraction alone.

In certain cases, the bioelectric stimulator is further programmed to produce a bioelectric signal (to produce SDF-1) of 30 pulses per second with a voltage of 3.5 mV, and successively alternating currents of 700 to 1500 picoamps for one minute, and again with 700 to 1500 picoamps for one minute, plus stimulated with a current of 0.25 mA, pulse duration of 40 pulses per second, pulse width of 100 μs, and frequency of 100 Hz, each signal for 40 minutes to 8 hours a day.

In certain cases, the bioelectric stimulator is further programmed to produce (to produce PDGF) a bioelectric signal of 3 V/cm, 10 Hz, 2 μA (0.000002 amps), and pulse duration of 0.2 ms. In certain cases, the bioelectric stimulator is further programmed to produce (to produce PDGF) a bioelectric signal of 20 V/cm, 100 Hz, 0.25 μA (2.5e-7 amps), and pulse duration of 40 pulses/s, width of 100 μs.

In certain cases, the bioelectric stimulator is further programmed to produce (to produce follistatin) a bioelectric signal of 10V at 50 Hz and 100 Hz, 0.25 mA for one (1) minute.

In certain cases, the bioelectric stimulator is further programmed to produce a bioelectric signal (to produce tropoelastin) of 0.06 V with 50 Hz alternating electrical field and electric current of 1 mA for 15 minutes and 3 mA for 15 minutes.

In certain cases, the bioelectric stimulator is further programmed to produce (for the expression of IGF-1) a bioelectric signal applied to the target tissue of 3 mV with electric frequency of 22 Hz, and current of 1 mA for 15 minutes and 3 mA for 15 minutes.

In certain cases, a method of using the bioelectric stimulator to stimulate tissue of a subject includes connecting (directly or wirelessly) the bioelectric stimulator to the target tissue or cells of the subject. The target tissue may be selected from, e.g., the group consisting of muscle, brain, kidney, pancreas, bone, tumor, and nerve.

In certain cases, the subject is interested in body building.

In certain cases, the subject has been diagnosed as suffering from kidney failure, diabetes, bone degeneration, aging, cancer, and/or immune system dysfunction.

In certain cases, the subject has age-related cognitive decline. In certain cases, the subject has cognitive decline resulting from a neurodegenerative disease. In certain cases, the subject has cognitive decline resulting from traumatic brain injury. In certain cases, the subject is receiving or has received radiation treatment or chemotherapy for cancer.

A preferred system includes: a bioelectric stimulator that controls/stimulates the release/production of Klotho by a target cell or tissue. The stimulator may be associated with (e.g., connected to) the organ or tissue to be treated with a pacing infusion lead (available from Nanoscribe of Eggenstein-Leopoldshafen, Germany) or wirelessly. In certain cases, the interface with the subject's tissue may be by a conductive soft wrap.

The stimulator can be designed to externally deliver all regeneration promoting signals wirelessly to the subject's organ(s), tissue(s), and/or cells. In certain embodiments, a micro infusion pump may be included in the system to deliver other supportive substances in greater volume more quickly.

While not intending to be bound by theory, the described system utilizes precise bioelectric signaling sequences that appear to communicate with DNA and cell membranes within stimulated tissues of the subject to cause the cells to produce high volumes of the Klotho protein. Potential indications include muscle regeneration and treatment, body building, kidney regeneration and treatment, brain regeneration and treatment, cognitive function and memory improvement, skin regeneration and treatment, wound healing, erectile dysfunction, eye regeneration and treatment, anti-aging, Multiple Sclerosis, lung regeneration and treatment, COPD, liver regeneration and treatment, hearing regeneration and treatment, blood pressure management, polyp treatment, cyst treatment, fibroid treatment, Cystic Fibrosis, heart failure, and heart valve decalcification.

BRIEF DESCRIPTION OF THE DRAWINGS

FIG. 14 is a table depicting the results of the Example.

DETAILED DESCRIPTION

In certain embodiments, described is a bandage wrap that is applied to the affected region. A micro-stimulator may be located conveniently in the bandage wrap and is utilized to distribute specific bioelectric signals to the affected tissue and nerves that regulate various protein expressions for stem cell homing, stem cell proliferation, stem cell differentiation, blood vessel formation, blood circulation improvement, muscle function repair, and DNA repair.

Figure 1:
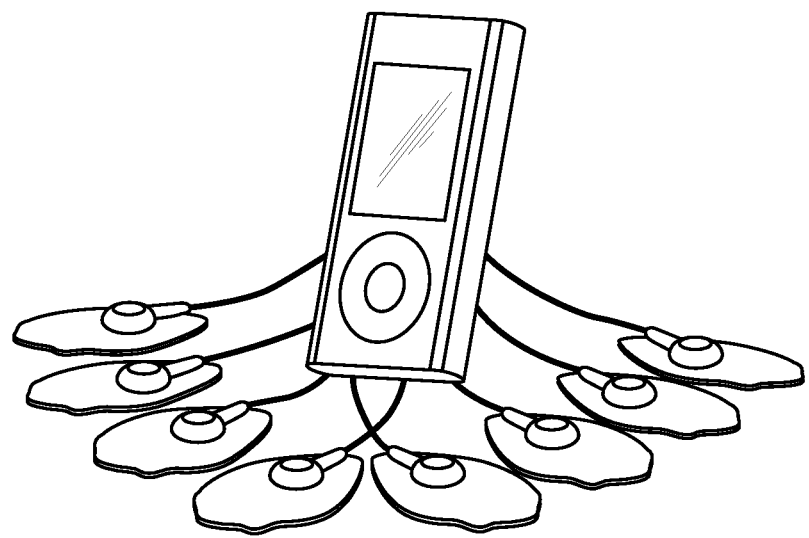
FIG. 1 depicts a programmed bioelectric stimulator for delivery to a subject connected to multiple soft conductive electrode pads.
Figure 2:
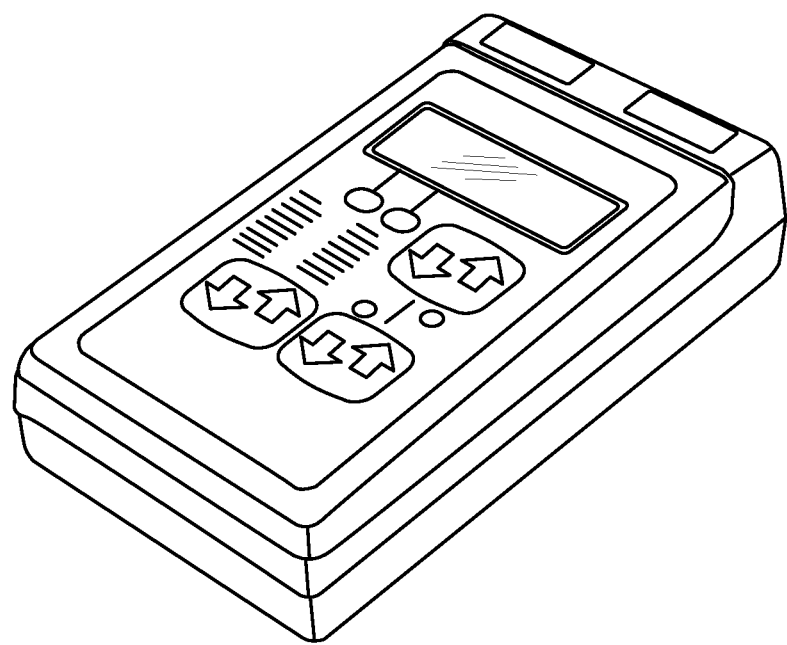
FIG. 2 depicts a programmed bioelectric stimulator as described herein.
Figure 3:
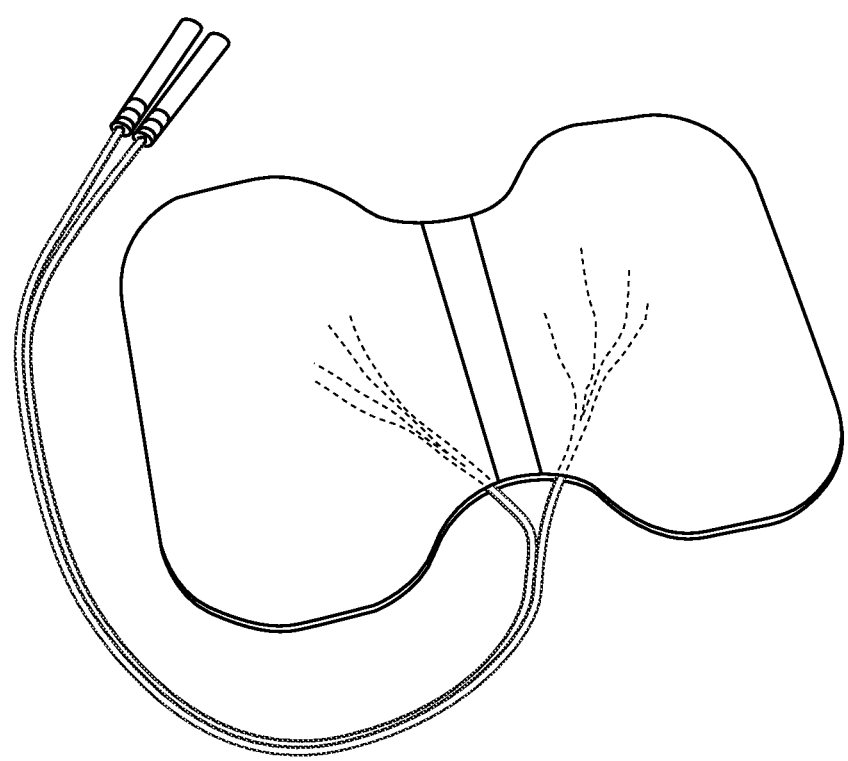
FIG. 3 depicts a conductive soft wrap for use with the system.
Figure 4:
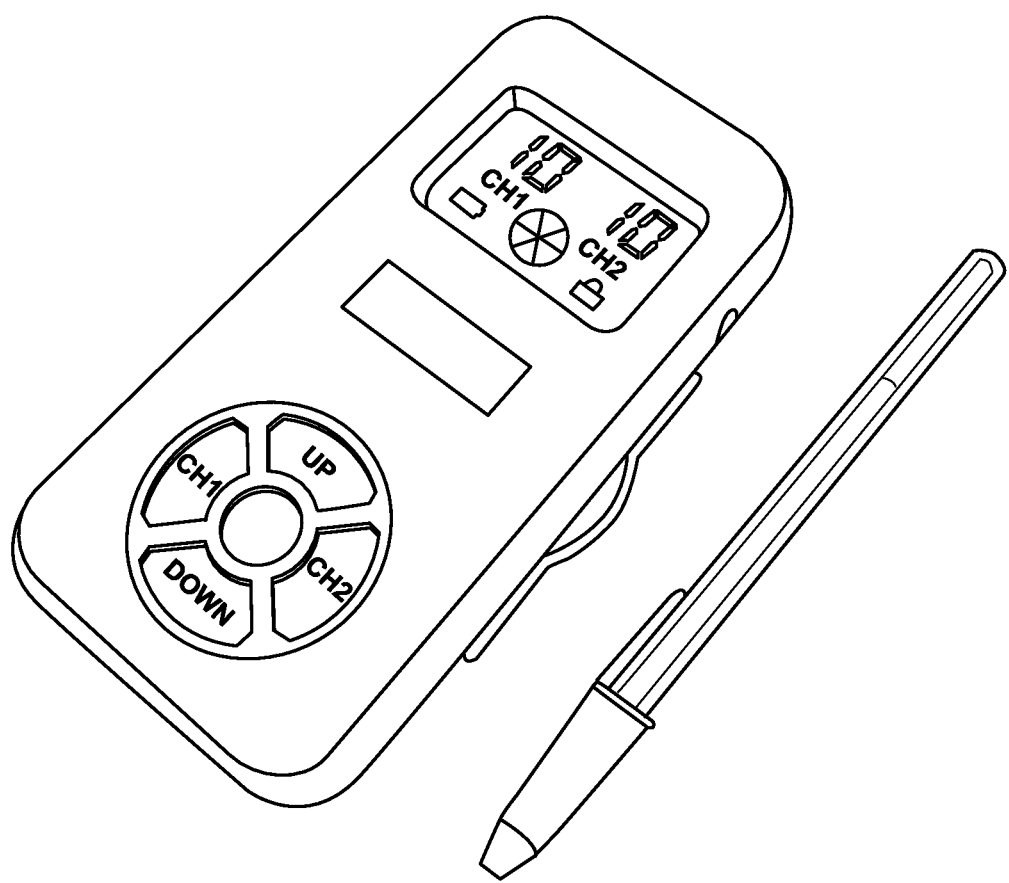
FIG. 4 depicts a programmed bioelectric stimulator depicted alongside a pen.

Referring now to FIG. 1, depicted is a stimulator for use in treating a human. The depicted device is about the size of a pen (FIG. 4) and is programmable.

Preferably, the system utilizes a bioelectric stimulator programmed to control expression and/or release of Klotho, SDF-1, IGF-1, PDGF, follistatin, and tropoelastin.

Klotho is as described above. Follistatin promotes muscle growth and counteracts myostatin. SDF-1 is generally for recruiting stem cells and maturing blood vessels. IGF-1 is for DNA repair. PDGF is a second stem cell homing factor and helps tissue regeneration. Any one of the protein expression signals work well on their own for organ regeneration, but they work better together. SDF-1 is a powerful regeneration protein, as is IGF-1.

The micro voltage signal generator may be produced utilizing the same techniques to produce a standard heart pacemaker well known to a person of ordinary skill in the art. An exemplary microvoltage generator is available (for experimental purposes from Cal-X Stars Business Accelerator, Inc. DBA Leonhardt's Launchpads or Leonhardt Vineyards LLC DBA Leonhardt Ventures of Salt Lake City, Utah, US). The primary difference is the special electrical stimulation signals needed to control, e.g., precise follistatin release on demand (which signals are described later herein). The leading pacemaker manufacturers are Medtronic, Boston Scientific Guidant, Abbott St. Jude, BioTronik and Sorin Biomedica.

Construction of the electric signal generators and pacemakers, are known in the art and can be obtained from OEM suppliers as well as their accompanying chargers and programmers. The electric signal generators are programmed to produce specific signals to lead to specific protein expressions at precisely the right time for, e.g., optimal organ treatment or regeneration.

The pacing infusion lead may be constructed or purchased from the same suppliers that build standard heart pacemaker leads. Pacing infusion leads may be purchased from a variety of OEM vendors. The pacing infusion lead may, for example, be a standard one currently used in heart failure pacing studies in combination with drug delivery.

An infusion and electrode wide area patch may be constructed by cutting conduction polymer to shape, and forming plastic into a flat bag with outlet ports in strategic locations.

Micro stimulators may be purchased or constructed in the same manner heart pacemakers have been made since the 1960's. When used with a micro infusion pump, such pumps can be purchased or produced similar to how they have been produced for drug, insulin, and pain medication delivery since the 1970's. The programming computer can be standard laptop computer. The programming wand customary to wireless programming wands may be used to program heart pacers.

Both wireless non-invasive and/or implantable wire lead ("electrode") based means may be used to deliver the regeneration and healing promoting bioelectric signals to target organs.

A wireless, single lumen infusion pacing lead or infusion conduction wide array patch may all be used to deliver the regeneration signals and substances to the organ of interest to be treated or they may be used in combination.

A re-charging wand for use herein is preferably similar to the pacemaker re-charging wand developed by Alfred Mann in the early 1970's for recharging externally implantable pacemakers.

Bioelectric stimulation can be done with the described microstimulator, which can have a pacing infusion lead with, e.g., a corkscrew lead placed/attached at, e.g., the center of the tissue to be stimulated and/or treated.

The microstimulator is actuated and runs through programmed signals to signal the release of, e.g., Klotho. In such a method, when the electrical signal includes (within 15%): a biphasic square pulse at 20 Hz, 0.1 V (100 mV), and a 7.8 ms pulse duration for 24 hours of stimulation (wherein the electrical signal is as measured three (3) mm deep into the tissue), the protein expressed and/or released is Klotho.

In such a method, when the electrical signal includes (within 15%): 10V at 50 Hz and 100 Hz for about 12 hours each (duration 1 minute) (wherein the electrical signal is as measured three (3) mm deep into the tissue), the protein further expressed and/or released by the cell is follistatin.

In such a method, when the electrical signal includes (within 15%): 3 mV with a frequency of about 22 Hz, and a current of about 1 mA for about fifteen (15) minutes and 3 mA for about fifteen (15) minutes (duration 5 minutes) (wherein the electrical signal is as measured three (3) mm deep into the tissue), the protein further expressed and/or released by the subject is IGF-1.

For example, upregulation of IGF-1, and SDF-1 was achieved in cardiomyocytes using such signals. Upregulation of SDF-1 was achieved in pig heart. It has been found that signals for one cellular tissue work with other cellular tissues too.

Also described is a method of activating a tissue to further produce stromal cell-derived factor 1 ("SDF-1"), the method including: stimulating the (e.g., human) tissue with an electrical signal, wherein the electrical signal includes (within 15%): 30 pulses per second with a voltage of about 3.5 mV, and successively alternating currents of about 700 to 1500 picoamps for about one minute, and again with 700 to 1500 picoamps for about one minute and stimulated with current of about 0.25 mA, pulse duration of about 40 pulses/s, pulse width of about 100 μs, wherein the electrical signal is as measured three (3) mm deep into the tissue. In such a method, the period of time is typically at least 24 hours. In such a method, the field strength is typically at least 0.1 V/cm.

What follows are preferred signals from the stimulator. For example, described are two PDGF expression control signals, one low voltage and one higher voltage. The test tissue is sheep heart tissue. The test cells are mesenchymal stem cells.

30% PDGF increase >3 V/cm, 10 Hz, 2 micro amps (0.000002 amps) and the pulse duration 0.2 ms.

230% PDGF increase >20 V/cm 100 Hz, 0.25 mA (2.5e-7 amps) and pulse duration of 40 pulses/s, width of 100 μs.

PDGF Signal: 20V for 1 minute, 20 mV for 10 minutes, current of 0.25 mA, pulse duration of 40 pulses/s, pulse width of 100 μs, and frequency of 100 Hz for 5 minutes followed by 528 Hz for 3 minutes and 432 Hz for 3 minutes and 50 Hz for 3 minutes.

SDF-1—Stem cell recruiting signal: 30 pulses per second with a voltage of 3.5 mV, and successively alternating currents of 700 to 1500 picoamps for one minute, and again with 700 to 1500 picoamps for one minute and stimulated with current of 0.25 mA, pulse duration of 40 pulses/s, pulse width of 100 μs, and frequency of 100 Hz—each signal for 40 minutes to 8 hours a day for 2 to 36 months as needed for ideal results. Duration 7 minutes.

Stem cell proliferation signals: 15 mV and a current of 500 picoamps at 70 pulses per minute for 3 hours and 20 pulses per minute, a pulse amplitude of from 2.5-6 volts, and a pulse width of from 0.2-0.7 milliseconds for 3 hours. Duration 3 minutes.

Follistatin—(muscle growth) production signal: 10V at 50 HZ and 100 HZ 0.25 mA. Duration 1 minute.

IGF-1: 3 mv with electric frequency of 22 Hz, and electric current of 1 mA for 15 minutes and 3 mA for 15 minutes. Duration 5 minutes.

An exemplary bioelectric signal sequence in humans (after Klotho) is as follows.

SDF-1 (stem cell homing signal)—5 minutes

IGF-1 signal (DNA repair)—3 minutes

Follistatin signal (myostatin antagonist) at 1 volt (not 10 volts) –3 minutes.

PDGF—1 minute

A week after treatment, samples can be collected for morphometric evaluation by in-situ hybridization or RT-PCR.

Among the accompanying figures are included images of the corresponding signals with the name, voltage, and frequency of each signal written on each image The signals are to be further defined in terms of current and frequency, not voltage and frequency as shown. The voltage delivered to the cells will be different for each tissue type, but with current all of the signals can be kept constant regardless of tissue type. The device should have a current driven signal (instead of voltage driven like most other devices).

Figure 5:
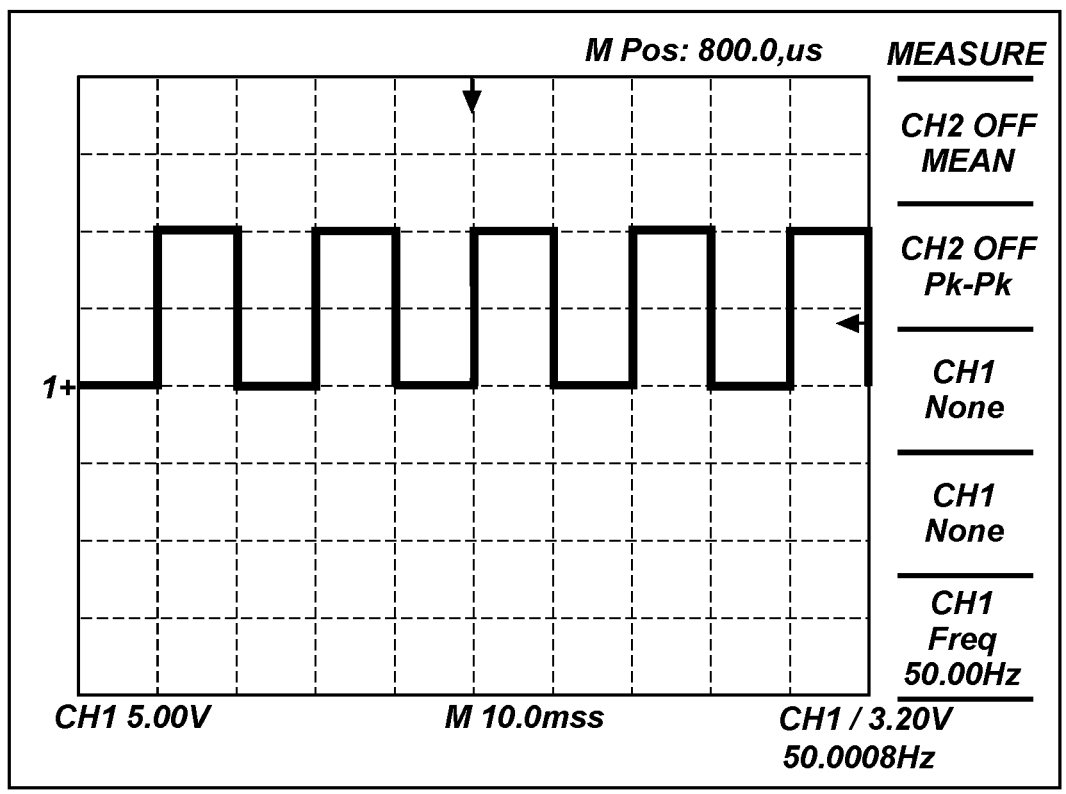
FIG. 5 depicts an image of the signal (voltage and frequency) associated with follistatin at 10V/cm, 50 Hz, square wave.

FIG. 5 depicts an image of the signal (voltage and frequency) associated with follistatin at 10V/cm, 50 Hz, square wave. Follistatin is a powerful antagonist of myostatin. Follistatin was first isolated from the ovary and is known to suppress follicle-stimulating hormone. The system has precise bioelectric signaling sequences that have demonstrated an ability to control release of the follistatin protein in target tissue on demand.

Figure 6:
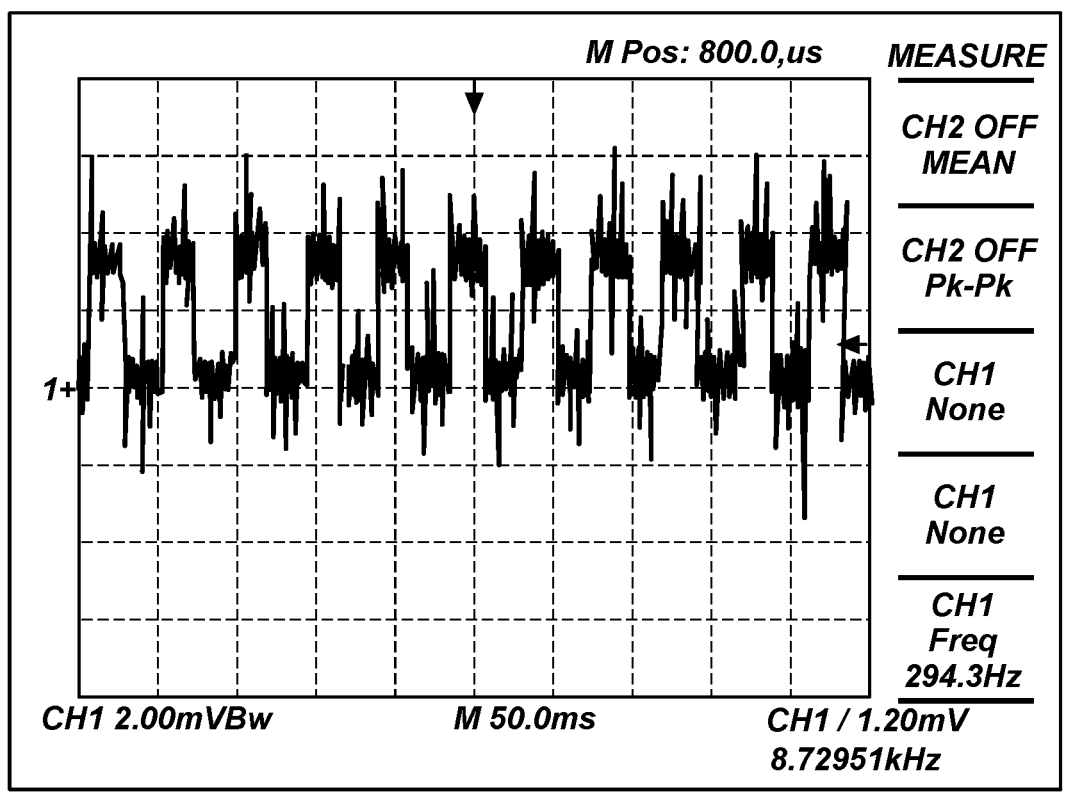
FIG. 6 depicts an image of the signal (voltage and frequency) associated with IGF-1: 3.0 mV, 22 Hz, square wave.

FIG. 6 depicts an image of the signal (voltage and frequency) associated with IGF-1: 3.0 mV, 22 Hz, square wave.

Figure 7:
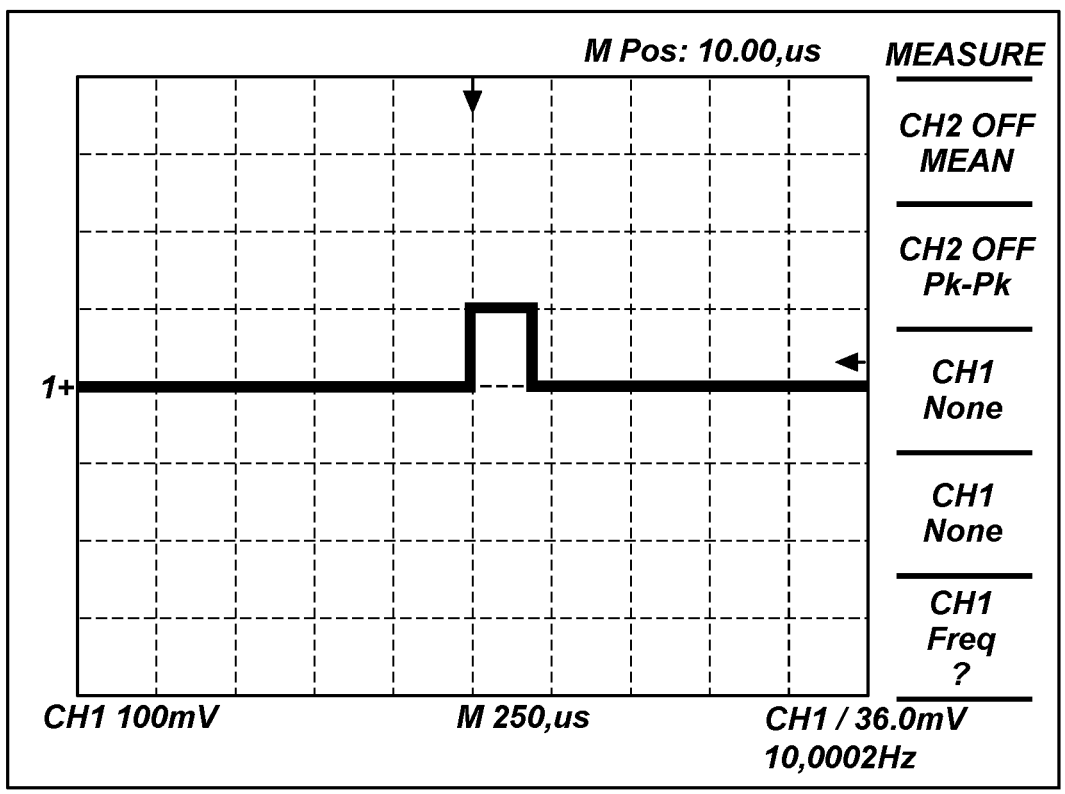
FIG. 7 depicts an image of a signal (voltage and frequency) associated with PDGF30%: 3V/cm (100 mV here), 10 Hz, pulse width 200 μs, square wave.
Figure 8:
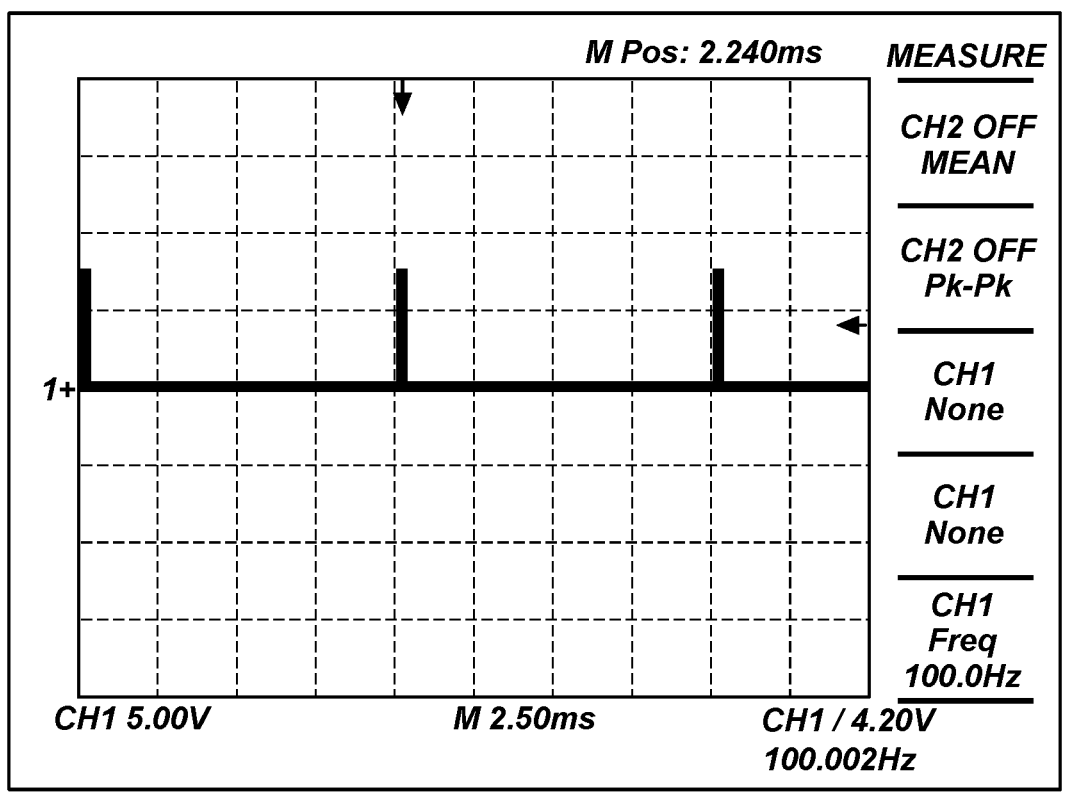
FIG. 8 depicts an image of a signal (voltage and frequency) associated with PDGF230%: 20V/cm (7.0V here), 100 Hz, pulse width 100 μs, square wave.

FIG. 7 depicts an image of the signal (voltage and frequency) associated with PDGF30%: 3V/cm (100 mV here), 10 Hz, pulse width 200 μs, square wave. FIG. 8 also depicts an image of the signal (voltage and frequency)

associated with PDGF230%: 20V/cm (7.0V here), 100 Hz, pulse width 100 µs, square wave.

Figure 9:
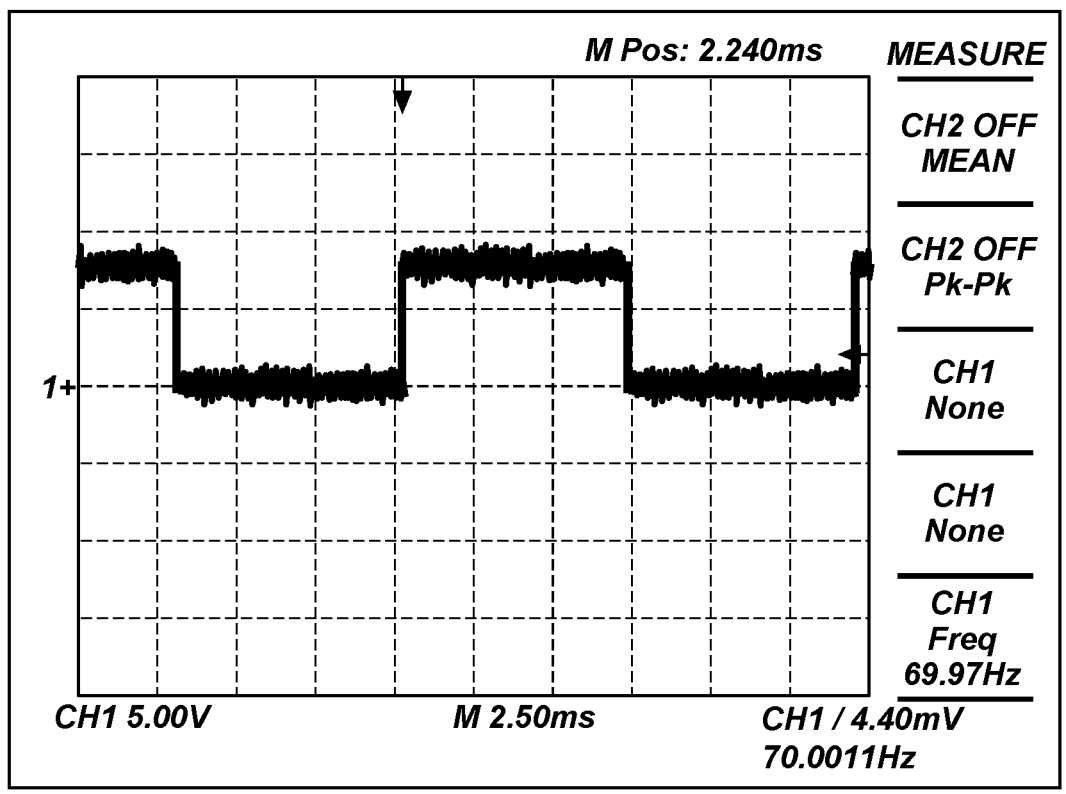
FIG. 9 depicts an image of a signal (voltage and frequency) associated with stem cell proliferation (or homing): 15 mV, 70 Hz, square wave.

FIG. 9 depicts an image of the signal (voltage and frequency) associated with stem cell proliferation: 15 mV, 70 Hz, square wave.

Figure 10:
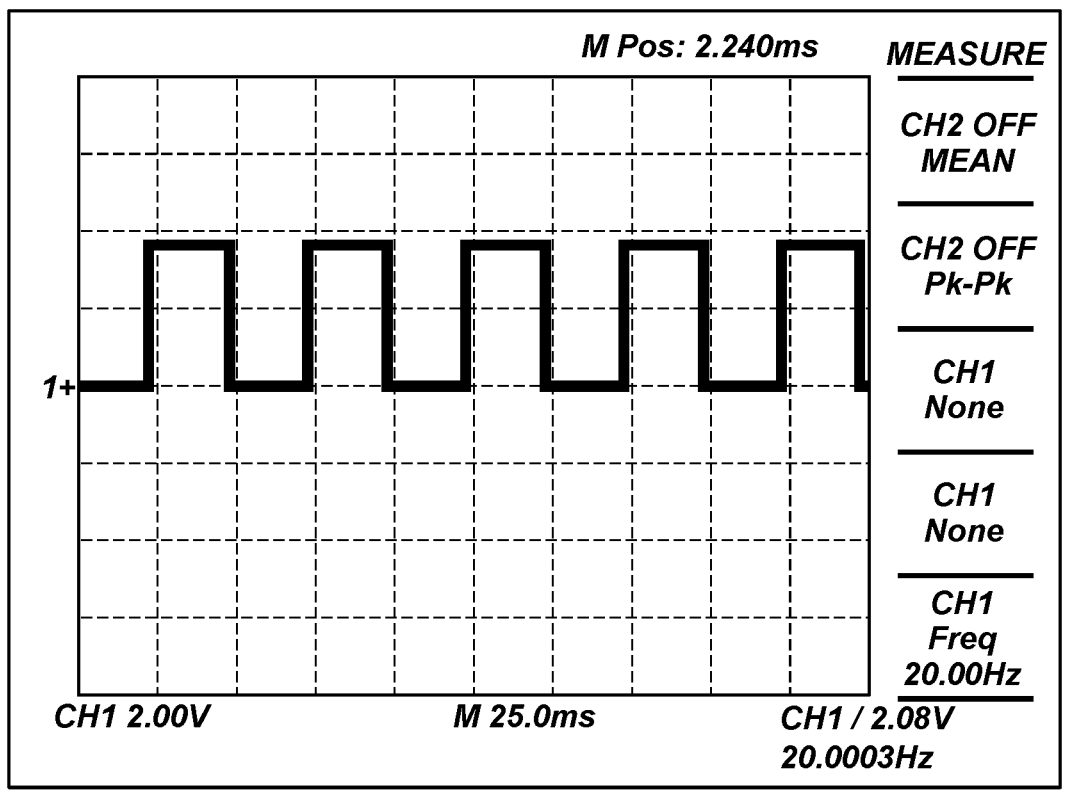
FIG. 10 depicts an image of a signal (voltage and frequency) associated with stem cell proliferation: 2.5-6.0 V (4V here), 20 Hz, pulse width 200-700 μs, square wave.

FIG. 10 depicts an image of the signal (voltage and frequency) associated with stem cell proliferation: 2.5-6.0 V (4V here), 20 Hz, pulse width 200-700 µs, square wave.

Figure 11:
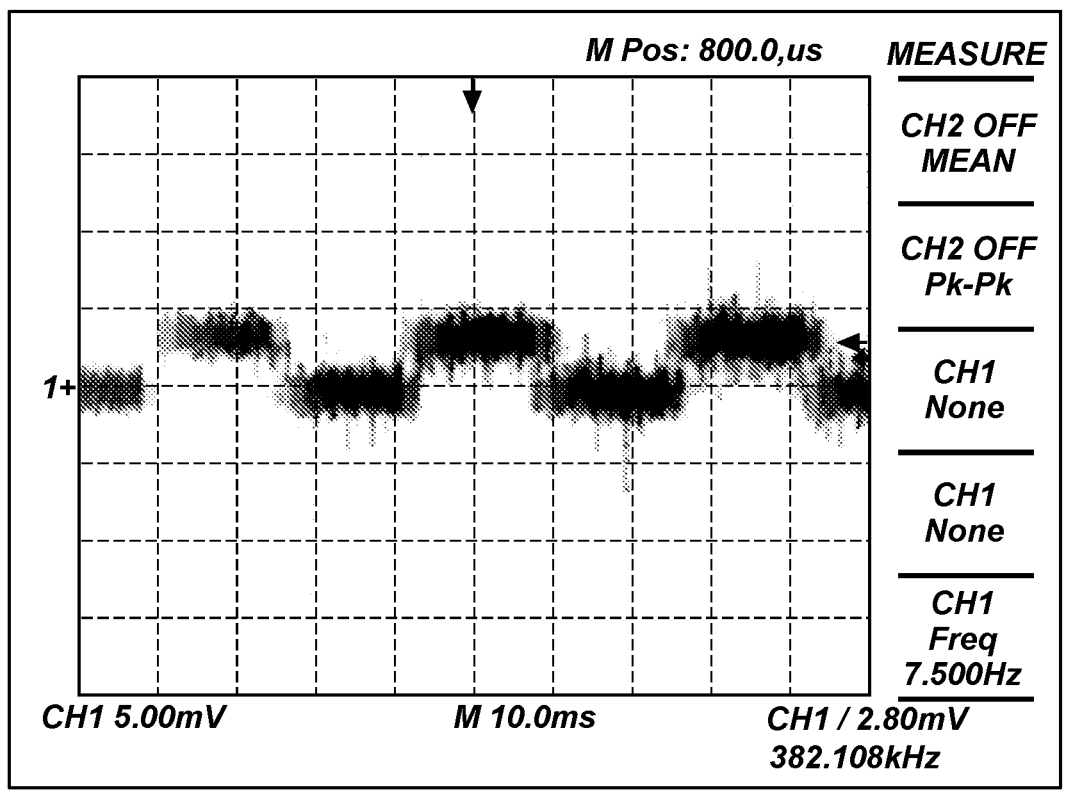
FIG. 11 depicts an image of the signal (voltage and frequency) associated with SDF-1: 3.5 mV, 30 Hz, square wave.

FIG. 11 depicts an image of the signal (voltage and frequency) associated with SDF-1: 3.5 mV, 30 Hz, square wave.

Figure 12:
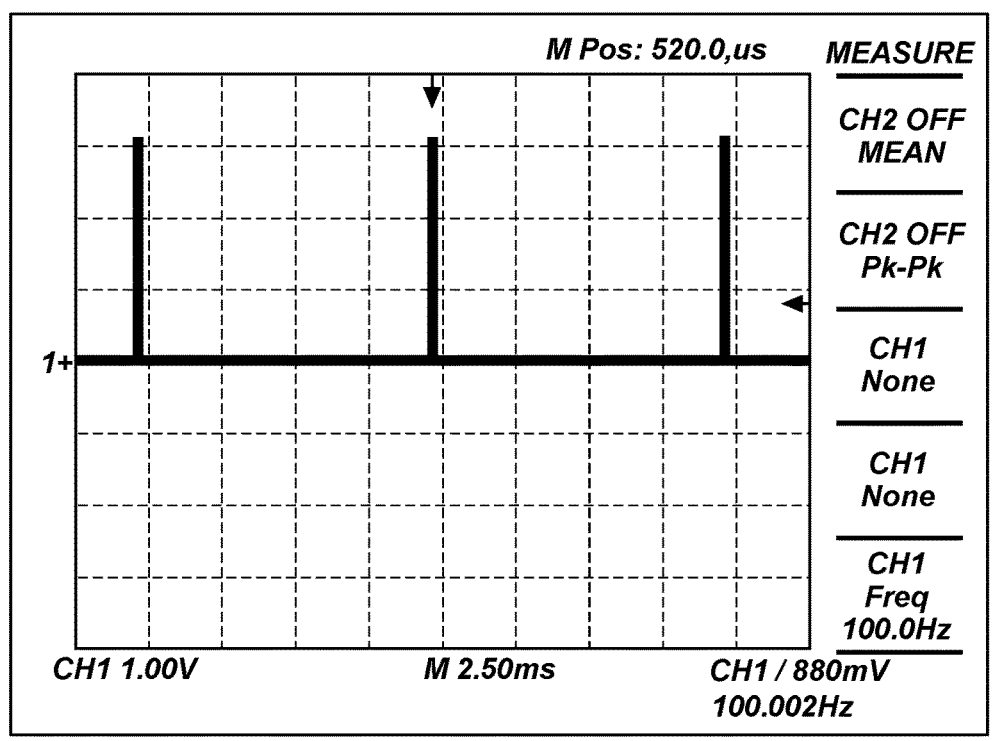
FIG. 12 depicts an image of the signal (voltage and frequency) associated with SDF-1 ($2^{nd}$ part): 0.25 mA (3.0V shown here), 100 Hz, 100 μs pulse width, square wave.

FIG. 12 depicts an image of the signal (voltage and frequency) associated with SDF-1 ($2^{nd}$ part): 0.25 mA (3.0V shown here), 100 Hz, 100 µs pulse width, square wave.

Figure 13:
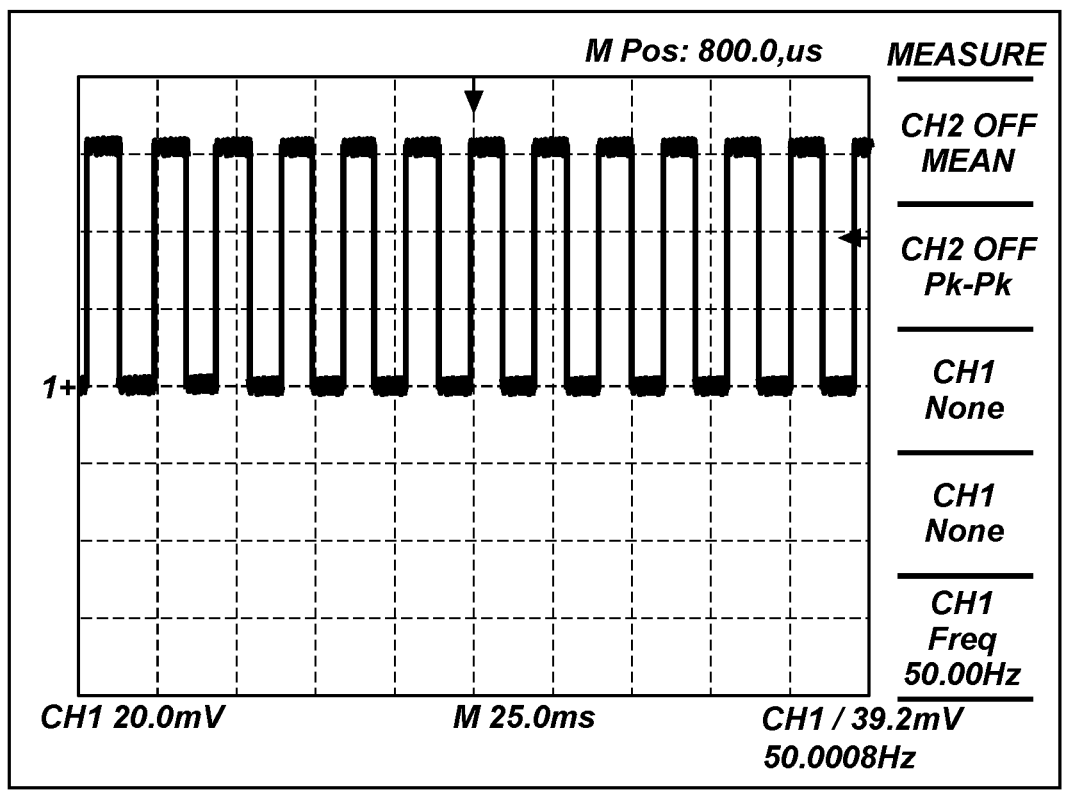
FIG. 13 depicts an image of the signal (voltage and frequency) associated with tropoelastin: 60 mV, 50 Hz, square wave.

FIG. 13 depicts an image of the signal (voltage and frequency) associated with tropoelastin: 60 mV, 50 Hz, square wave.

Relationship Between The Components:

The micro voltage signal generator is attached to the pacing infusion lead with, e.g., a corkscrew tip, deep vein stimulation lead (Medtronic) (e.g., for bioelectric stimulation of the brain), or conductive polymer bandage or patch to the tissue or organ to be treated. An external signal programmer may be used to program the micro voltage signal generator with the proper signals for treatment including the Klotho producing signal. The device battery may be re-chargeable with an external battery charging wand.

The essential elements are the micro voltage signal generator and the means for delivering the signal to the target tissue.

The signal generator may be external or internal. The transmission of the signal may be wireless, via liquid and/or via wires.

The tissue contact interface may be, e.g., a patch or bandage or may be via electrodes or leads. FDA cleared gel tape electrodes (Mettler) may be used for skin delivery. Electro acupuncture needles may be used to ensure the signals positively reach target tissues under the skin.

In certain embodiments, a subject's organ(s) and/or tissue(s) are first scanned or analyzed with a device to determine what his or her needs may be before treatment begins. The scanning/analysis can be by, e.g., generating mechanical vibrations at position adjacent the location to be an analyzed as described in, e.g., US 2003/0220556 A1 to Porat et al. (the contents of which are incorporated herein by this reference) and/or by measuring transmembrane voltage potential of a cell (see, e.g., Chernet & Levin, "Transmembrane voltage potential is an essential cellular parameter for the detection and control of tumor development in a *Xenopus* model," *Dis. Models & Mech.* 6, pp. 595-607 (2013); doi:10.1242/dmm.010835, the contents of which are also incorporated herein by this reference. See, also, Brooks et al. "Bioelectric impedance predicts total body water, blood pressure, and heart rate during hemodialysis in children and adolescents" J. Ren Nutr., 18(3):304-311 (May 2008); doi: 10.1053/j.jrn.2007.11.008, the contents of which are incorporated herein by this reference, describing the use of bioelectric impedance to evaluate the variability of blood pressure, systolic blood pressure, etc.

As used herein, "scanning" means measuring bioelectrical electrical activity of organs, sometimes by placement of a bion coil reader and transmitter in the organ, and direct that information to a computer. The computer stores the bioelectrical read measurements of diseased organs and healthy organs and makes a comparative exam classifying the organ into one category or another, which is much like a doctor using information to make a diagnosis.

Presently, the best approach for whole body and individual organ scanning is to use a combination of: a. 3D Body Scannint, b. Quantum Magnetic Resonance Scanning, c. Biofeedback scanning, d. Bioelectric scanning, e. Bion implant scanning, f Nervous system scanning, and g. Light activated cell reaction reading.

Scanners such as the Ina'Chi scanner, the Quantum Magnetic Resonance Analyzer (QMRA), the 3D Quantum Health Analyzer Scan whole body organ health 2, Body-Scan® scanner, and the "BIONic muscle spindle" are also useful.

For example, the subject is positioned for analysis with a device, preferably with a non-invasive testing device for evaluating, e.g., the autonomic nervous system, organ function(s), and risk factors associated with heart disease, diabetes, and stroke. The non-invasive testing device may analyze data from, e.g., the subject's skin galvanic response, skin color, oximeter, blood pressure, and body composition analyzer to determine hardening and thickening of the subject's arteries, the subject's heart health, exercise capacity, thyroid function, neurotransmitter balance, and multiple other markers for health. See, also, Fatemi et al. "Imaging elastic properties of biological tissues by low-frequency harmonic vibration" *Proceedings of the IEEE*, 91(10):1503-1519 (October 2003).

In an alternative embodiment, the analysis conducted by the device comprises (or further includes) detecting minute energy fields around the human body with, e.g., a "SQUID magnetometer" (SQUID is an acronym for "Superconducting Quantum Interference Device"), able to detect biomagnetic fields associated with physiological activities in the subject's body. A quantum resonant magnetic analyzer analyzes such fields. The magnetic frequency and energy of a subject's organ(s) and/or tissue(s) are collected by appropriately positioning the sensor with respect to the portion of the subject's organ(s) and/or tissue(s) to be analyzed, and after amplification of the signal by the instrument, the data are compared with standard quantum resonant spectrum of diseases, nutrition, and other indicators/markers to determine whether the sample waveforms are irregular using a Fourier approach.

Treatment may include, e.g., moving magnets or changing magnetic fields (pulsed electromagnetic fields) about the tissue and/or organ, for example, to reduce inflammation or treat pain or induce tissue growth in the subject.

The invention is further described with the aid of the following illustrative Example.

EXAMPLES

Example—Controlling Expression and/or Release of Klotho

Twelve samples of gingiva cells were stimulated with a biphasic square pulse at 20 Hz, 0.1 V (100 mV), and a 7.8 ms pulse duration for 24 hours of stimulation. The cells were gingival fibroblasts from a 28 year old Caucasian male (atcc.org/en/Products/All.CRL-2014.aspx), which were passaged less than 8 times. RT-PCR was used to measure results before and after the described bioelectric stimulation. Results: Klotho expression up an average of 248% (n=5) and as high as 465% (see FIG. 14).

REFERENCES (The Contents of the Entirety of Each of Which is Incorporated Herein by this Reference.)

Prochazka et al. "Cocktail of Factors from Fat-derived Stem Cells Shows Promise for Critical Limb Ischemia" sciencenewsline.com/news/2016012204520017.html (Jan. 21, 2016).

Salcedo et al. "Low current electrical stimulation upregulates cytokine expression in the anal sphincter," *Int. J. Colorectal Dis.*, 2012 February; 27(2):221-5. doi: 10.1007/s00384-011-1324-3. Epub (October 2011).

Hopkins Medicine "Overview of Pacemakers and Implantable Cardioverter Defibrillators (ICDs)," hopkinsmedicine.org/healthlibrary/conditions/cardiovascular dis-eases/overview_of_pacemakers_and_implantable_cardioverter_defibrillators_icds_85,P00234/.

Columbia "Implant Procedure Concepts—Pacemaker, ICD and CRT Overview," columbia.edu/itc/hs/medical/hickey/docs/Pacemaker,%20ICD %20and %20CRT %20Overview %2 0022007.pdf

What is claimed is:

1. A bioelectric stimulator comprising an electric signal generator and electrodes, which electric signal generator is programmed to produce a bioelectric signal that stimulates target tissue comprising living cells to express and/or release Klotho polypeptide by the living cells of the target tissue, wherein the bioelectric signal comprises, within 15%, a biphasic pulse at 20 Hz and 7.8 ms pulse duration.

2. The bioelectric stimulator of claim 1, wherein the bioelectric stimulator is further programmed to produce, within 15%, a bioelectric signal of 30 pulses per second, and successively alternating currents for one minute, and again for one minute, plus stimulated with a pulse of 40 pulses per second, pulse width of 100 µs, and frequency of 100 Hz.

3. The bioelectric stimulator of claim 1, wherein the bioelectric stimulator is further programmed to produce a bioelectric signal of 10 Hz and pulse duration of 0.2 ms.

4. The bioelectric stimulator of claim 1, wherein the bioelectric stimulator is further programmed to produce a bioelectric signal of 100 Hz, pulse of 40 pulses/s, and pulse width of 100 µs.

5. The bioelectric stimulator of claim 1, wherein the bioelectric stimulator is further programmed to produce, within 15%, a bioelectric signal of 50 Hz and a bioelectric signal of 100 Hz.

6. The bioelectric stimulator of claim 1, wherein the bioelectric stimulator is further programmed to produce a bioelectric signal of 50 Hz alternating electrical field.

7. The bioelectric stimulator of claim 1, wherein the bioelectric stimulator is further programmed to produce, within 15%, a bioelectric signal with frequency of 22 Hz.

8. A method of using a bioelectric stimulator to stimulate target tissue comprising living cells of a subject, wherein the bioelectric stimulator comprises an electric signal generator and electrodes, and wherein the electric signal generator is programmed to produce a bioelectric signal comprising, within 15%, a biphasic pulse at 20 Hz and 7.8 ms pulse duration, the method comprising:

connecting the bioelectric stimulator to the target tissue of the subject via the electrodes, and actuating the bioelectric stimulator to produce the programmed bioelectric signal(s) signal so as to stimulate the living cells to express and/or release klotho polypeptide.

9. The method according to claim 8, wherein the target tissue is selected from the group consisting of muscle, brain, kidney, pancreas, bone, tumor, and nerve.

10. The method according to claim 8, wherein the subject has been diagnosed as suffering from kidney failure, diabetes, bone degeneration, aging, cancer, and/or immune system dysfunction.

11. The method according to claim 8, wherein the subject has age-related cognitive decline, cognitive decline resulting from a neurodegenerative disease, and/or cognitive decline resulting from traumatic brain injury.

12. The method according to claim 8, wherein the subject is receiving or has received radiation treatment or chemotherapy for cancer.

13. A method of treating a cell, the method comprising:
stimulating the cell to express and/or release Klotho polypeptide by applying a bioelectric signal to the cell, wherein the bioelectric signal comprises, within 15%, a biphasic pulse at 20 Hz and 7.8 ms pulse duration.

14. The method according to claim 13, further comprising stimulating the cell by applying a further bioelectric signal to the cell, wherein the further bioelectric signal comprises 30 pulses per second and successively alternating currents for one minute, and again for one minute, plus stimulated with a pulse of 40 pulses per second, pulse width of 100 µs, and frequency of 100 Hz.

15. The method according to claim 13, further comprising stimulating the cell by applying a further bioelectric signal to the cell, wherein the further bioelectric signal is 10 Hz and pulse duration of 0.2 ms.

16. The method according to claim 13, further comprising stimulating the cell by applying a further bioelectric signal to the cell, wherein the further bioelectric signal comprises 100 Hz and pulse of 40 pulses/s, and pulse width of 100 µs.

17. The method according to claim 13, further comprising stimulating the cell by applying a further bioelectric signal to the cell, wherein the further bioelectric signal comprises, within 15%, 50 Hz and another bioelectric signal of 100 Hz.

18. The method according to claim 13, further comprising stimulating the cell by applying a further bioelectric signal to the cell, wherein the further bioelectric signal is 50 Hz alternating electrical field for 15 minutes.

19. The method according to claim 13, further comprising stimulating the cell by applying a further bioelectric signal to the cell with a frequency of, within 15%, 22 Hz, for 15 minutes.

20. The method according to claim 13, wherein the cell is comprised within a subject.

21. The method according to claim 20, wherein the subject has been diagnosed as having kidney failure, diabetes, bone degeneration, aging, cancer, and/or immune system dysfunction.

* * * * *